US005759596A

United States Patent [19]
Domingues et al.

[11] Patent Number: 5,759,596
[45] Date of Patent: Jun. 2, 1998

[54] YEAST-LEAVENED REFRIGERATED DOUGH PRODUCTS

[75] Inventors: David J. Domingues, Plymouth; William A. Atwell, Andover; William P. Pilacinski, Maple Grove, all of Minn.

[73] Assignee: The Pillsbury Company, Minneapolis, Minn.

[21] Appl. No.: 735,152

[22] Filed: Oct. 24, 1996

Related U.S. Application Data

[63] Continuation of Ser. No. 366,601, Dec. 29, 1994, abandoned, which is a continuation of Ser. No. 829,453, Jan. 31, 1992, abandoned, which is a continuation-in-part of Ser. No. 732,081, Jul. 18, 1991, abandoned.

[51] Int. Cl.$^6$ .............................. A21D 8/04; A21D 10/02; A21D 4/00; C12N 1/18
[52] U.S. Cl. .................... 426/8; 426/19; 426/27; 426/62; 435/255.1; 435/255.2; 435/254.21
[58] Field of Search ................... 426/8, 19, 27, 426/62; 435/255.1, 255.2, 254.21

[56] References Cited

U.S. PATENT DOCUMENTS

| Re. 28,074 | 7/1974 | Smerak et al. . |
| 1,232,758 | 7/1917 | Blacklock . |
| 2,043,139 | 6/1936 | Wille et al. . |
| 2,333,764 | 11/1943 | Burgeson . |
| 2,478,618 | 8/1949 | Armstrong et al. ............. 426/128 |
| 3,096,178 | 7/1963 | Tucker . |
| 3,348,951 | 10/1967 | Evans . |
| 3,635,733 | 1/1972 | Kiehline et al. . |
| 3,649,304 | 3/1972 | Fehr et al. . |
| 3,876,815 | 4/1975 | Kurzius ............................ 426/19 X |
| 3,934,046 | 1/1976 | Weaver et al. ....................... 426/418 |
| 3,939,001 | 2/1976 | Clausi et al. ..................... 426/576 X |
| 3,995,066 | 11/1976 | Muys et al. . |
| 4,000,321 | 12/1976 | Mochizuki et al. .................. 426/5 |
| 4,001,445 | 1/1977 | Horrocks et al. .................. 426/250 |
| 4,020,188 | 4/1977 | Forner ............................. 426/94 |
| 4,341,871 | 7/1982 | Langejan ......................... 426/62 X |
| 4,346,115 | 8/1982 | Clement et al. . |
| 4,381,315 | 4/1983 | Yong et al. . |
| 4,406,911 | 9/1983 | Larson et al. . |
| 4,450,177 | 5/1984 | Larson et al. ...................... 426/19 |
| 4,500,548 | 2/1985 | Silva . |
| 4,522,832 | 6/1985 | Morrison . |
| 4,547,374 | 10/1985 | Nokatomi et al. . |
| 4,693,898 | 9/1987 | Nakatomi et al. . |
| 4,792,456 | 12/1988 | Katz et al. . |
| 4,966,778 | 10/1990 | Benjamin et al. . |

FOREIGN PATENT DOCUMENTS

| 2055052 | 5/1992 | Canada . |
| 0145367 | 6/1985 | European Pat. Off. . |
| 0305071 | 3/1989 | European Pat. Off. . |
| 0442575 | 8/1991 | European Pat. Off. . |
| 0487878 | 6/1992 | European Pat. Off. . |
| 384114 | 12/1932 | United Kingdom . |
| 1007280 | 10/1965 | United Kingdom . |
| 1587296 | 4/1991 | United Kingdom . |

OTHER PUBLICATIONS

"Carbon and Phosphate Utilization", M. Johnston and M. Carlson, in The Molecular and Cellular Biology of the Yeast Saccharomyces, 1992, pp. 200–210.

"Induction of Galactokinase in *Saccharomyces cerevisiae*: Kinetics of Induction and Glucose Effects", B. Adams, Journal of Bacteriology, Aug. 1972, vol. 111, No. 2, pp. 308–315.

"Catabolite Repression", Boris Magasanik, Cold Spring Harbor Symp. Quant. Biol. 26, pp. 249–256.

Hino et al., "New Freeze–Tolerant Yeast for Frozen Dough Preparations", 6031 Cereal Chemistry 64(4):269–275, 1987.

Finney, "A Review of Older and Some Newer Short–Time Bread Baking Studies," The Bakers Digest, vol. 51, No. 5, Oct. 1977, pp. 81–86.

Harrison, et al., "Phosphlipid in Baker's Yeast During Drying", Nature [200] pp. 1189–1190 (1963).

Herrera, et al., "Loss of Cell Constituents On Reconstitution of Active Dry Yeast", Arch. Biochem. and Biophys. [63] 131–143 (1956).

Autio, et al., Frozen Doughs: Rheological Changes and Yeast Viability, 1992, Cereal Chemistry, vol. 69, No. 4, 1992, pp. 409–413.

Pyler, Baking Science & Technology, 3rd Ed., vol. 1, 1988, pp. 204–209.

Wolt, et al., Factors Involved in the Stability of Frozen Dough. II. The Effects of Yeast Type, Flour Type, and Dough Additives on Frozen–Dough Stability, 1984, Cereal Chemistry, vol. 61, No. 3, pp. 213–221.

Empty Packet of Red Star Active Dry Yeast, with instructions for use rehydration (experiment date of Oct. 15 1994; purchased March 1994).

Singh, et al., "Growth Analysis of Mutations Affecting Growth of *Saccharomyces Cerevisiae* at Low Temperature", Genetics 77:651–659 (Aug., 1974).

Ursic, et al., "A Cold–Sensitive Mutant of *Saccharomyces Cerevisiae* Defective in Ribosome Processing", Molec. gen. Genet. 175, 313–323 (1979).

*Primary Examiner*—Donald E. Czaja
*Assistant Examiner*—Choon P. Koh
*Attorney, Agent, or Firm*—Janal M. Kalis; Aleya Rahman

[57] ABSTRACT

The present invention provides refrigeratable yeast-leavened dough compositions and methods of making such doughs. In a first embodiment, a dough composition of the invention is made by rehydrating dried yeast at chilled temperatures, which causes selective lysing (a loss in the selectivity of the yeast plasma membrane). Such a dough composition exhibits a cold sensitivity in that the yeast is capable of leavening the dough at elevated temperatures, but becomes inactive at refrigeration temperatures. In another embodiment, the dough composition and the strain of yeast used therein are chosen to limit the total leavening action of the yeast by controlling the amount of substrate in the dough fermentable by the yeast. In a third embodiment, a dough comprises a mixture of flour, water and a mutant yeast which is low temperature sensitive. Such an "lts" yeast is active at elevated temperatures, but becomes substantially inactive at refrigeration temperatures. Dough compositions made in accordance with any of these embodiments of the invention are capable of being leavened at elevated temperatures, yet stored in a sealed container at refrigeration temperatures for extended periods of time.

9 Claims, 24 Drawing Sheets

YEAST-LEAVENED REFRIGERATED DOUGH PRODUCTS

This is a continuation of prior application Ser. No. 08/366,601, filed Dec. 29, 1994, now abandoned, which application is a continuation of application Ser. No. 07/829,453, filed Jan. 31, 1992, now abandoned, which is a continuation-in-part of application Ser. No. 07/732,081, filed Jul. 18, 1991, now abandoned.

FIELD OF THE INVENTION

The present invention relates to dough compositions for use in making edible baked goods. In particular, the invention provides a yeast-leavened dough which can be stored at refrigeration temperatures.

BACKGROUND OF THE INVENTION

Yeast has been used to leaven dough for bread and the like for, quite literally, thousands of years. The presence of yeast in a dough composition imparts a particular aroma and flavor to the finished product which is widely associated with high-quality bread, pastries and other baked goods.

In producing refrigerated doughs commercially, typically a large batch of dough is made and the dough is divided into smaller portions. These smaller portions are commonly placed in individual sealable containers for subsequent sale to consumers. In many instances, the dough portions are leavened in these containers in a process known as "proofing." The containers are designed in such a way as to allow the lid to act as a gas vent for a head space of air which is left above the unleavened dough. The dough is then leavened under controlled conditions so that it expands to fill the container and effectively seal the lid. This leavening is often continued until a positive pressure of about 15-20 psi is attained within the container, at which time the leavening action must cease. If the leavening were to continue significantly beyond this point, the pressure within the container could exceed acceptable safety limits and cause the container to rupture. These containers may then be shipped and stored for later sale and use. Such commercially produced doughs are commonly refrigerated in order to extend their shelf life; a minimum acceptable shelf life for most commercial applications is deemed to be about 90 days.

In dough compositions, the yeast culture generally continues to grow and produce carbon dioxide until the dough is baked, requiring rather precise control over the leavening conditions in order to produce a consistent product. Even at refrigeration temperatures, which generally range between about 0° C. and 12° C., yeast cultures in doughs remain active and continue to produce carbon dioxide. Accordingly, when yeast is used as the leavening agent in a dough, carbon dioxide pressure within a sealed storage container can relatively quickly build to a level which causes the containers to rupture or explode. In order to produce a refrigerated dough product with a shelf life of at least 90 days, dough manufacturers have therefore been effectively unable to use yeast as a leavening agent in commercial refrigerated dough products.

Dough manufacturers have been forced to replace yeast in doughs with chemical leavening agents, such as baking soda or the like. Such chemical leavening agents generally comprise a combination of a leavening acid (e.g., citric acid or glucono delta lactone (GDL)) and a leavening base (e.g., bicarbonate of soda). The acid and base portions of these leavening agents react with one another to generate carbon dioxide gas within the dough, causing the dough to increase in volume, or "rise." One of the primary advantages of such leavening agents is that their behavior is based upon a predictable chemical reaction, permitting one to readily control the volume of carbon dioxide produced to leaven the dough. Once the chemical reaction of the leavening agents has proceeded to completion, carbon dioxide production ceases.

This permits commercial dough manufacturers to produce a product with an extended shelf life without having to worry about the continuing leavening action which would occur with yeast as a leavening agent. However, it is widely agreed that the taste and texture of a dough which has been leavened with chemical leavening agents is noticeably inferior to yeast-leavened products. In order to simulate the desirable taste and aroma of yeast-leavened dough products, yeast flavoring, such as inactive pasteurized yeast cultures, is often added to the chemically leavened dough. Nonetheless, products made from such doughs still lack the characteristic flavor associated with yeast leavening. Additionally, such flavorings do not change the fact that chemically leavened refrigerated dough yields a product which has an inferior texture and a significantly lower specific volume than typical yeast-leavened products.

For these reasons, there has been a long-felt need in the field for a yeast-leavened dough product which may be refrigerated for extended periods of time. However, despite this acutely-felt need, experimenters have been unable to develop a dough composition in which yeast provides the necessary leavening action to leaven the dough and proof the storage container, yet substantially cease carbon dioxide production at refrigeration temperatures for extended storage of the dough product.

SUMMARY OF THE INVENTION

The present invention provides methods of making refrigeratable yeast-containing doughs. In a first method, the yeast is active at elevated temperatures so that the dough may be controllably proofed or leavened, but substantially ceases activity at refrigeration temperatures. This permits extended storage of the dough at refrigeration temperatures without rupturing the containers within which the dough is stored. As used herein, the term "inactive" as applied to yeast means that the leavening action of the yeast is substantially stopped, as indicated by the fact that very little or no carbon dioxide is produced in the dough at refrigeration temperatures.

A first method of making such dough comprises rehydrating dried yeast, such as active dry yeast (ADY) or instant dry yeast (IDY), in water at a temperature of no greater than about 10° C. and mixing the cold-rehydrated yeast with with other components of the dough, which may include flour, water, and a variety of other ingredients. After mixing, the resulting dough may be placed into containers and proofed at an elevated temperature. After it has been cooled, the dough may be stored at refrigeration temperatures for 90 days or more without any substantial likelihood of rupturing a container due to an increase in carbon dioxide pressure therein.

This embodiment of the present invention also contemplates a yeast-containing dough composition which can be refrigerated for extended periods of time. Such a composition includes dried yeast, chilled water, and flour, and additional ingredients may be added for flavoring and the like. The yeast in a dough of the invention will remain substantially inactive at refrigeration temperatures.

In another embodiment of the invention, a specific strain of yeast and dough composition are chosen so that the total amount of sugar or sugars fermentable by the yeast in the dough is limited. By so doing, one may limit the maximum volume of carbon dioxide which the yeast can generate. This in turn prevents generation of sufficient carbon dioxide to rupture a sealed container of dough even if the temperature of the dough is inadvertently elevated.

In yet another embodiment of the invention, a dough comprises a mixture of flour, water and a "low temperature sensitive" yeast. Such yeast, referred to as "lts" yeast, behaves substantially the same as normal strains of yeast under elevated temperature conditions, such as during the proofing process. However, the lts yeast responds to a decrease in temperature. In particular, such yeasts become substantially inactive, and hence substantially cease producing carbon dioxide, at refrigeration temperatures. This dough composition may be placed into containers and proofed and the containers may then be sealed to provide a refrigeratable dough product.

A method according to this embodiment of the present invention comprises making such a dough and holding the dough at refrigeration temperatures. Flour, water and lts yeast are mixed together to form the dough. The method may also include the additional steps of placing the resultant dough in a pressurizable container and heating the dough within the container to an elevated temperature for proofing. Once the dough in the container has been proofed, the temperature of the dough within the container is reduced to refrigeration temperatures and the dough is stored at refrigeration temperatures for an extended period of time. A method of this embodiment may also further comprise the step of removing the dough from the container and baking it to produce a baked good.

DETAILED DESCRIPTION OF THE PREFERRED EMBODIMENTS

Figure 1:
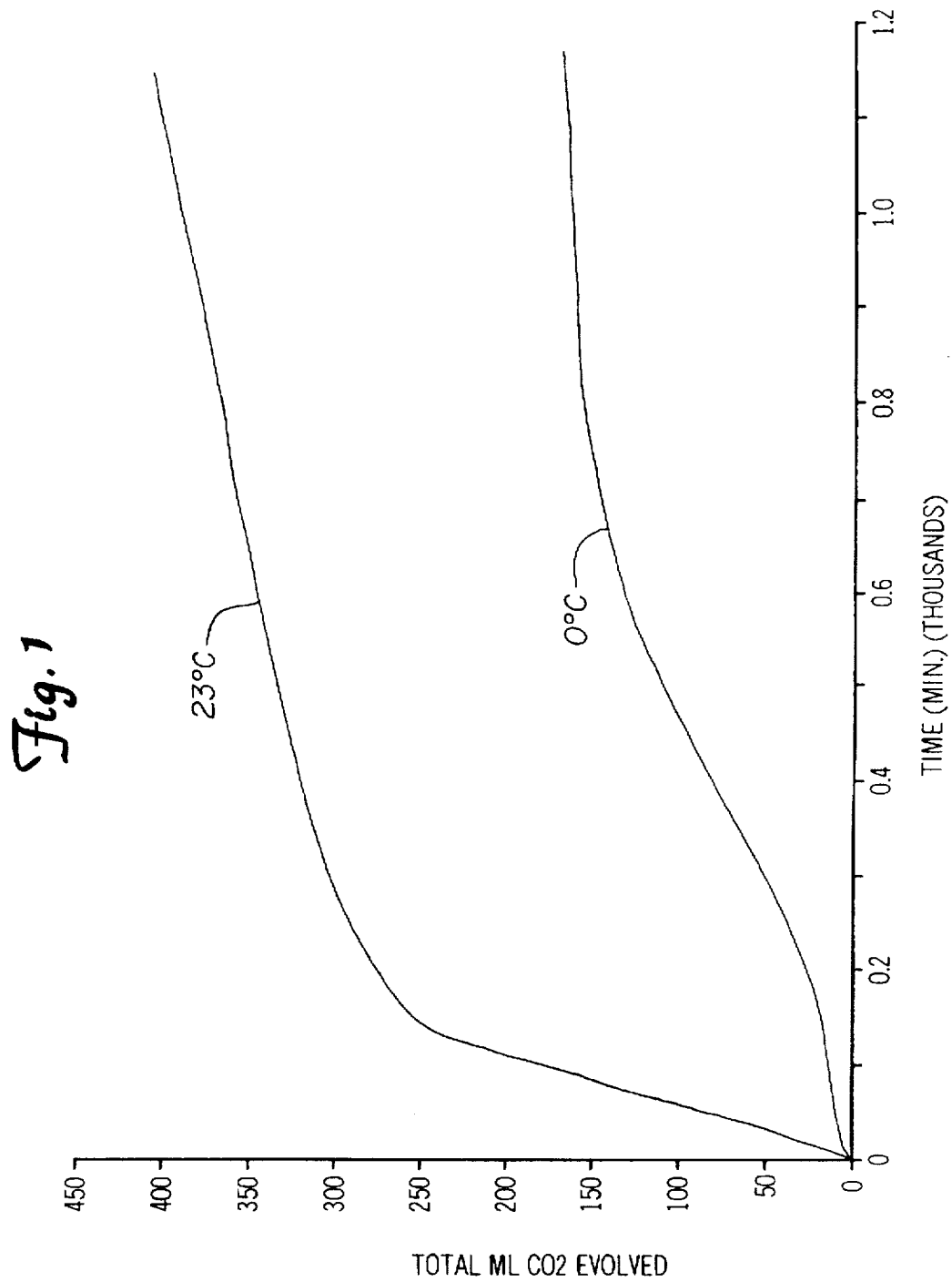
FIG. 1 is a graph comparing the volume of carbon dioxide generated by yeast rehydrated at 0° C. and at 23° C.

The present invention contemplates methods of making a dough composition which may be stored for extended periods of time at refrigeration temperatures. In a first embodiment, a dried yeast is first obtained. Dried yeast for use in the invention may be, for instance, active dry yeast, which most commonly has a moisture content of approximately 6–8%, or instant dry yeast (IDY), which generally has about 3–6% moisture content. This dried yeast is then added to an amount of chilled water at least sufficient to rehydrate the dried yeast. The water is desirably no greater than about 10° C., and is preferably about 0° C. The amount of water used may be significantly more than the minimum amount necessary to rehydrate the yeast. In a preferred embodiment, the amount of water to which the yeast is added is sufficient to satisfy the water requirements of the intended dough composition to which the yeast and water are added. This ensures proper dispersion of the yeast in the dough composition when the dough is mixed. The yeast and water may be mixed to form a slurry to uniformly disperse the yeast in the water.

Once the yeast and water have been in contact for a period of time, desirably 10–15 minutes, to insure a proper degree of rehydration of the yeast, the additional components of the dough composition may be mixed with the yeast-water slurry. Most of the remaining ingredients tend to be dry powders or the like and include a significant proportion of a flour product, such as ground wheat. Ingredients necessary to achieve a desired texture or taste in the final, cooked dough product may be added at this stage as well. Such ingredients will most commonly include things such as salt, sugars, wheat gluten, or other flavorings. These ingredients should be thoroughly mixed together to insure a uniform dough composition, as is known in the art. Any of a wide variety of conventional mixing techniques may be used.

A dough composition so formed is capable of being refrigerated for extended periods of time. If so desired, the dough may be immediately stored at refrigeration temperatures, which tend to be between 0° C. and 12° C. with a range of about 4° to 7.2° C. being preferred. Storing the dough in this manner holds the yeast in an inactive state wherein it substantially ceases production of carbon dioxide. When it is desired to use the dough, a suitable amount of the dough may be heated to an elevated temperature, i.e., a temperature above refrigeration temperatures. Such an elevated temperature may be approximately room temperature, but it is preferred that a slightly higher temperature, e.g., on the order of about 30°–40° C. be used, as this will tend to accelerate the activity of the yeast, and hence shorten the time necessary to leaven the dough. Once the dough is sufficiently leavened, it may be immediately placed in an oven for baking.

Alternatively, the dough composition formed as outlined above may be held at an elevated temperature for a predetermined period of time to permit the yeast to leaven the dough shortly after the dough composition has been mixed. The dough is desirably held at an elevated temperature for a sufficient period of time to provide the desired degree of leavening of the dough composition. Once the dough has been leavened, it may then be stored at refrigeration temperatures to hold the yeast in its inactive state.

This process appears to be particularly useful in commercial dough manufacturing operations, where small quantities of dough are individually packaged and proofed in sealed containers. Once the dough has been proofed within the container, the container may be stored for an extended period of time at refrigeration temperatures, such as in refrigerated trucks during transportation and in the refrigerated food case at a grocery store. When it is desired to bake the dough, such as when a consumer purchases a container of refrigerated dough and intends to bake the dough at home, the container may simply be opened and the leavened dough is ready to be baked immediately.

In one embodiment of the present invention, a refrigerated dough composition is prepared which generally includes flour and water in suitable proportions, along with dried yeast rehydrated in chilled water in a sufficient amount to leaven the dough. The dough composition will have the unique ability to be stored at refrigeration temperatures for extended periods of time without generating any significant amount of carbon dioxide.

When active dry yeast is rehydrated in accordance with commonly accepted procedures, it is slurried with water which is held at room temperature or above, most commonly between 35° C. and 40° C. After allowing a sufficient time for the yeast to rehydrate, e.g., about 10–15 minutes, the yeast-water slurry is mixed with flour and any other ingredients which one may desire to add to the dough composition.

Yeast used in a dough composition of this invention, however, is rehydrated in chilled water. The temperature of the water is desirably no greater than about 10° C.; and preferably iced water, i.e., liquid water held at 0° C., will be used. Suitable proportions of dry yeast and chilled water are mixed together to form a slurry, and this slurry is held for a sufficient time, such as 10–15 minutes, before the slurry is mixed with the other ingredients of the dough.

The amount of water used in the slurry should be at least sufficient to rehydrate the dried yeast. Thus, at least about 3 to 4 ml of water should be added to the slurry for each gram of yeast. In a preferred embodiment, however, the water used in the slurry is enough to constitute the entire water requirement of the desired dough composition. In this manner, the yeast-water slurry can be directly mixed with the other dough ingredients in the desired proportions without necessitating the addition of further water to reach the intended dough composition.

As explained in some detail in connection with the illustrative examples set forth below, rehydrating active dry yeast in chilled water yields a yeast culture which differs significantly from active dry yeast rehydrated in accordance with the prior art. Studies have shown that upon drying, the plasma membrane of a yeast cell loses its selectivity and subsequently becomes permeable to compounds which do not freely traverse the plasma membrane of a non-dried yeast cell. Moreover, rehydration at lower temperatures is a slow process, thus allowing the escape of numerous soluble low molecular weight intracellular compounds (hereinafter referred to as "selective lysis").

Desirably, to produce a suitable yeast culture for use in the present invention about 95% of the yeast cells in the rehydrated yeast-water slurry of the invention should be selectively lysed, i.e., have "leaky" plasma membranes which are unable to reduce methylene blue dye. Acceptable results were obtained using yeast cultures in which 97% to 99% of the cells had been selectively lysed. A yeast culture in which substantially all of the yeast cells have been selectively lysed may yield acceptable results when added to a dough composition in accordance with this invention. It is preferred that at least about 1% of the yeast cells in the yeast-water slurry remain viable.

Any of a wide variety of species of yeast can be used in the present invention. It is generally preferred, though, that the species be of either the saccharomyces or kluyveromyces genus, as such yeasts are the most common in bread dough manufacturing and are therefore more thoroughly understood. One particularly preferred species is S. cerevisiae, commonly known as brewer's or baker's yeast. A number of different strains of this species, with each strain having different substrate preferences, is known in the art.

By rehydrating active dry yeast in chilled water in accordance with the present invention, the ability of the yeast to ferment sugars is unexpectedly sensitized to cold ambient temperatures. Once the chilled yeast-water slurry is mixed with the other ingredients of the dough, the yeast remains sufficiently active to leaven the dough at elevated temperatures, but the yeast remains inactive when the dough is maintained at refrigeration temperatures.

This cold inactivity property permits one to proof or leaven the dough to the desired degree at elevated temperatures, then hold the leavened dough at refrigeration temperatures for extended periods of time. Such extended storage will not significantly change the volume of the dough because the yeast is inactive and does not generate additional carbon dioxide. This unique property allows a commercial dough manufacturer to controllably leaven or proof dough and place it in a sealed container for sale to consumers at a later date. So long as the dough is stored at refrigeration temperatures until it is sold, the pressure in the container should not substantially increase over time. Even if the dough is temporarily warmed above refrigeration temperatures, as during improper transportation or storage, if it is chilled back down, any leavening action brought on by the elevated temperatures should be arrested and the yeast should once again become inactive.

In a second embodiment of the invention a refrigerated dough product is prepared wherein the dough composition and the yeast used therein are chosen to limit the total leavening action of the yeast by controlling the amount of substrate in the dough fermentable by the yeast. Certain strains of yeast which do not ferment certain sugars are known in the art; often, two different strains of the same species of yeast are unable to ferment the same sugars. Therefore, a strain of yeast may be utilized in a dough composition which is capable of fermenting only certain sugars. By controlling the total amount of those sugars in the dough composition the amount of fermentation can be regulated.

Wheat flours used in most commercial dough manufacturing operations contain about 5wt. % of damaged starch. Alpha-and beta-amylases (inherent in wheat flour) convert such starch into maltose, which is a sugar fermentable by many strains of yeast. If all of the maltose in a dough composition made with such flours is fermented by yeast, the volume of carbon dioxide produced will be on the order of five times the volume necessary to leaven the dough. In one embodiment of the present invention, the flour used in the dough composition may be processed to remove approximately 80% of the damaged starch before it is mixed with the other ingredients of the dough. By so limiting the source of the fermentable maltose, one can essentially starve the yeast once it has fermented all of the available substrate and produced the desired volume of $CO_2$.

Reducing the damaged starch content of a flour, though, may not be very reproducible and can add significantly to the cost of the flour. Hence, in a preferred embodiment, a strain of yeast which does not ferment maltose, referred to as "maltose negative," or just "MAL-," is chosen. Such yeasts can usually ferment other types of sugars, such as sucrose or dextrose, and the amount of sugar in the dough fermentable by the yeast can be accurately controlled to yield reproducible leavening results.

A wide range of yeasts which ferment sucrose but not maltose ("SUC+/MAL-") are commercially available, including the following strains of *S. Cerevisiae*: DZ (CBS 109.90), DS 10638 (CBS 110.90), DS 16887 (CBS 111.90) V 79 (CBS 7045), and V 372 (CBS 7437). The total amount of fermentable sugar in the dough can be adjusted to ensure that the volume of $CO_2$ gas produced by fermentation of the entire fermentable sugar supply is not unduly high. Approximately 50–100 ml of $CO_2$ per 100 grams of dough at 32° C. is usually sufficient, and the amount of fermentable sugar in the dough necessary to generate that volume of $CO_2$ will be determined on a case-by-case basis because it will vary with each strain of yeast.

As explained above, even at refrigeration temperatures, most yeast will generate $CO_2$. If the sugar substrate fermentable by the yeast is limited, carbon dioxide generation will stop when the sugar is exhausted. Hence, by either controlling the sugar content of the dough, or by allowing the yeast to metabolize the fermentable sugars in the dough for a given period of time prior to canning, $CO_2$ generation by the yeast can be substantially terminated once a certain predetermined volume has been reached, regardless of the temperature of the dough. Accordingly, the total volume of $CO_2$ generated in the container can be prevented from reaching a level sufficient to rupture the container.

A dough composition according to a third embodiment of the invention includes flour and water combined with a mutant strain of yeast which is low temperature sensitive. Such low temperature sensitive yeasts are characterized by the fact that they behave essentially normally at elevated temperatures but become essentially dormant or inactive at refrigeration temperatures. Such yeasts desirably comprise genetic mutations of normal strains of yeast. Normal strains of yeast are believed to contain a certain percentage of such yeast cells, and these lts mutants of the yeast may be isolated in any of a variety of methods.

For instance, cold sensitive mutants of the yeast may be isolated by tritium suicide enrichment as described by Littlewood and Davies in "Enrichment for Temperature-Sensitive and Auxotrophic Mutants in *Saccharomyces cerevisiae* by Tritium Suicide", *Mutat. Res.* Vol. 17. pp. 315–322 (1973), the teachings of which are incorporated herein by reference. In this tritium suicide enrichment process, a strain of yeast, which is preferably *S. cerevisiae*, is placed in a growth medium at normal temperatures and the temperature is then reduced to refrigeration temperatures. Once the yeast has reached the lower temperature, tritiated uridine or tritiated amino acids may be supplied to the culture. Those cells which continue to remain active at these lower temperatures incorporate these precursors and are killed off by the tritium. Low temperature sensitive mutants present in the yeast sample, though, will not incorporate the uridine or the amino acids because they remain substantially inactive at the lower temperature. Accordingly, the lts mutants preferentially survive the reduced temperature storage.

Some researchers in the field of genetics have investigated certain properties of these yeasts. For instance, Ursic and Davies reported the results of certain studies in "A Cold-Sensitive Mutant of *Saccharomyces cerevisiae* Defective in Ribosome Processing", *Molec. Gen. Genet.* 175, 313–323 (1979), and Singh and Manney discuss the results of their testing in "Genetic Analysis of Mutations Affecting Growth of *Saccharomyces cerevisiae* at Low Temperature", *Genetics*, 77:651–659 (August 1974); the teachings of these articles are incorporated herein by reference.

There appear to be a relatively large number of genes in yeast which can mutate to prevent the growth of the yeast at low temperatures. For purposes of the present invention, though, it does not appear to be critical which of these genes is affected in the mutant which is utilized. The important factor in selecting a yeast is that the yeast should remain active at elevated temperatures, such as room temperature, yet become substantially inactive and substantially cease carbon dioxide production at refrigeration temperatures.

In making a dough composition of the invention, such a lts yeast is mixed with water and a flour product, such as ground wheat, in suitable proportions to form a dough which is suitable for baking. Additional ingredients necessary to achieve a desired texture or taste in the final, cooked dough product may be added during this mixing as well. Such ingredients will most commonly include such things as salt, sugars, wheat gluten, or other flavorings. All of these ingredients should be thoroughly mixed together to ensure a uniform dough composition; a wide variety of means for mixing doughs are well known in the art and need not be discussed in detail here.

Such a dough composition is capable of being refrigerated for extended periods of time. If so desired, the dough may be immediately stored at refrigeration temperatures, which tend to be between about 0° C. and about 12° C., with about 4°–7.2° C. being preferred, without any proofing or leavening step. Storing the dough in this manner holds the yeast in an inactive state wherein it substantially ceases production of carbon dioxide. When it is desired to use the dough, a suitable amount of the dough may be heated to an elevated temperature, i.e., a temperature above refrigeration temperatures. This elevated temperature may be approximately room temperature, but it is preferred that a slightly higher temperature, e.g., on the order of about 30°–40° C. be used, as this will tend to accelerate the activity of the yeast and shorten the time necessary to leaven the dough. Once the dough is sufficiently leavened, it may be immediately placed in an oven for baking.

Alternatively, a dough composition of this embodiment, formed as outlined above, may be held at an elevated temperature for a predetermined period of time to permit the yeast to leaven the dough shortly after the dough composition has been mixed. This period of time should be sufficient to provide the entire desired degree of leavening of the dough composition. Once the dough has been sufficiently leavened or proofed, it may then be stored at refrigeration temperatures to hold the yeast in its inactive state.

As in the above embodiment utilizing yeast which is rehydrated in chilled water, the process of the present embodiment appears to be particularly useful in commercial dough manufacturing operations, where small quantities of dough are individually packaged and proofed in sealed containers. The proofed container may be stored for an extended period of time at refrigeration temperatures, such as in refrigerated trucks during transportation and in the refrigerated food case at a grocery store. When it is desired to bake the dough, such as when a consumer purchases a container of refrigerated dough and intends to bake the dough at home, the container may simply be opened and the leavened dough is ready to be baked immediately.

The inactivity of the lts yeast at refrigeration temperatures permits one to predictably proof or leaven the dough to the desired degree at elevated temperatures, then hold the leavened dough at refrigeration temperatures for extended periods of time. Such extended storage will not significantly change the volume of the lts yeast-leavened dough because the yeast is inactive and does not generate any significant volume of additional carbon dioxide. As in the cold-rehydrated yeast embodiment, this allows a commercial dough manufacturer to controllably leaven or proof dough and place it in a sealed container for sale to consumers at a later date. So long as the dough is stored at refrigeration temperatures until it is sold, the pressure in the container should not substantially increase over time. Even if the dough is temporarily warmed above refrigeration temperatures, as during improper transportation or storage, if it is chilled back down, leavening action brought on by the elevated temperatures should be arrested and the yeast should once again become inactive.

The following examples are intended to illustrate some of the specific characteristics and advantages of the present invention.

EXAMPLE 1

Two dough compositions were made, with one dough composition including active dry yeast rehydrated at 0° C., and the other including active dry yeast rehydrated at 23° C. In each case, 20 grams of active dry yeast of the species saccharomyces cerevisiae was added to 796.2 ml of water; in one batch, the water was held at a room temperature of 23° C., and in the other batch the water was iced and maintained at approximately 0° C. As the total weight of the intended dough composition was 2 kg, the 20 grams of yeast translates to 1 weight percent (wt. %) and the water constituted 39.81 wt. % of the intended total weight. The yeast and water were slurried together and held together for 15 minutes.

Each of the yeast-water slurries was then added to a McDuffy mixing bowl, and the following dry ingredients added: 1090.6 grams (54.53 wt. %) of wheat flour, 78.2 grams (3.91 wt. %) of wheat gluten pre-blend, and 15 grams (0.75 wt. %) of salt. The wheat gluten pre-blend was 75 wt. % vital wheat gluten, 21.9 wt. % hard, high gluten, enriched ingredient flour, 2.50 wt. % xanthan gum, and 0.616 wt. % azo. premix azodicarbonamide. The ingredients were mixed slowly for 30 seconds, followed by a more rapid rate of mixing for 8.5 minutes. The dough composition containing yeast rehydrated in chilled water reached its maximum consistency in approximately 5 minutes, while the yeast rehydrated at an elevated temperature reached its maximum consistency approximately 6 minutes after mixing began. The 0° C. rehydrated yeast-containing dough showed a much more rapid decrease in consistency after reaching its maximum than did the dough containing yeast rehydrated at 23° C.

After mixing was completed, a 50 gram sample of each of the two different dough compositions was placed in a Risograph, a machine manufactured by Sheldon Manufacturing, Inc. for detecting the volumetric amount of carbon dioxide generated in the leavening of doughs. These two dough samples were incubated in the Risograph at 32° C. for 19 hours.

Figure 2:
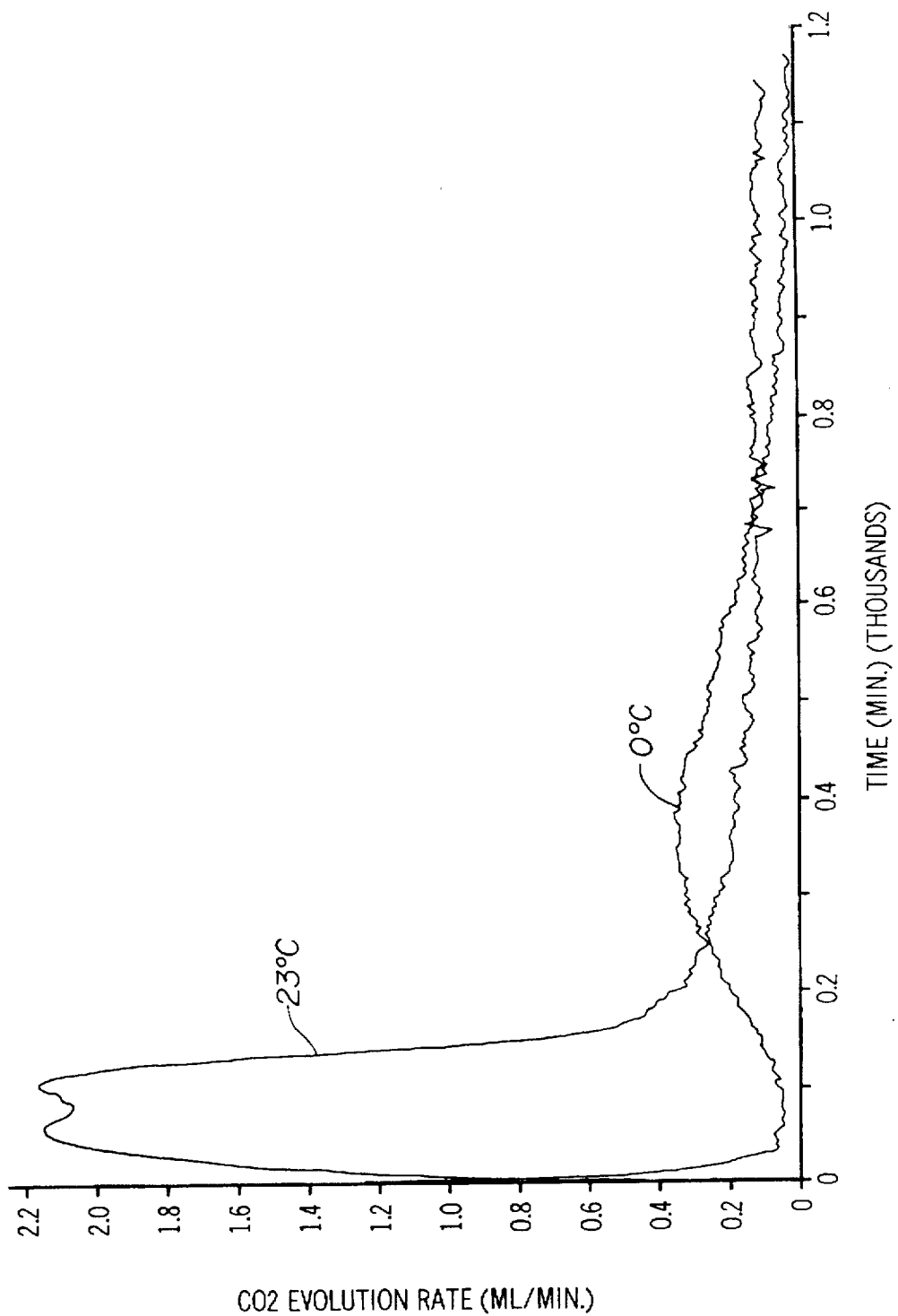
FIG. 2 is a graph showing the rate of carbon dioxide evolution of the rehydrated yeast cultures of FIG. 1.

FIGS. 1 and 2 show the results of the Risograph testing. FIG. 1 shows the total volume of carbon dioxide generated by each of the two samples as a function of time, and FIG. 2 shows the rate of carbon dioxide generation of the samples over time. The dough sample containing the warm-rehydrated yeast generated about 400 total ml of carbon dioxide gas, whereas the same size sample of a dough composition containing chilled-rehydrated yeast generated only about 160 ml of carbon dioxide. Thus, the total carbon dioxide generated by the dough composition according to the present invention was less than 40% of the total carbon dioxide produced by the other sample.

Additionally, as shown in FIG. 2, the rate of carbon dioxide evolution in the 0° C.-rehydrated sample showed a very short increase followed by a drop to almost zero and a generally bell-shaped curve wherein the maximum rate of carbon dioxide production was on the order of 0.35 ml per minute, after which it declined to a rate approaching 0 ml/minute. This is in marked contrast to the plot showing the rate of carbon dioxide generation by the standard dough sample, which showed a rapid, vigorous generation of carbon dioxide for the first two hours or so, with a maximum rate of about 2.1 ml of carbon dioxide per minute. Both this and the total carbon dioxide volume generation figures indicate that the damaged yeast cells in the sample rehydrated at 0° C. were unable to completely recover from the selective lysing which occurred during the chilled rehydration step.

Two samples of the remaining portions of each of the dough compositions, with each sample ranging between about 260 and about 270 grams, were baked under normal conditions. These dough samples were sheeted, rolled and sealed into separate containers, as is well known in the art of commercial dough manufacturing. The products were proofed in these containers at about 35° C. until a can pressure of about 15–20 psi was attained. The products were subsequently removed from the containers and baked at 350° F. for approximately 30 minutes.

The pressure in two containers filled with dough containing 23° C.-rehydrated yeast were 25 psi and 22 psi, respectively, while the pressure within two containers filled with 0° C.-rehydrated samples were 20 psi and 17.5 psi, respectively. One of the two dough compositions containing 23° C.-rehydrated yeast had a specific volume of 4.00 cc/g while the other had a specific volume of 4.23 cc/g. The 0° C.-rehydrated samples yielded a significantly lower specific volume, with one sample being at 3.26 cc/g while the other was at 3.29 cc/g.

The 23° C.-rehydrated yeast produced a greater pressure within the sealed containers than did the 0° C.-rehydrated yeast, which is commensurate with the data depicted in FIGS. 1 and 2, which clearly show that the 23° C.-rehydrated composition is capable of generating significantly more carbon dioxide in a shorter period of time. The specific volumes of the two pairs of samples also indicate that less carbon dioxide may have been generated during the proofing stage and that dough conditioning agents (such as glutathione) were released into the dough composition of the 0° C.-rehydrated yeast product, as either or both of these factors would tend to result in a more dense finished product with a lower specific volume.

Informal sensory analysis of the baked samples also indicated noticeable differences between the two dough compositions. Despite the fact that both compositions were baked for the same length of time under the same conditions, the dough composition of the present invention yielded an exterior which was golden brown in color, while the bread containing 23° C.-rehydrated yeast was pale yellow in color. The darker, more appealing baked color of the bread of the invention appears to have been due to the release of various proteinaceous substances released by the selectively lysed yeast cells; such substances will tend to add to Maillard browning during baking. Despite the differences in density and exterior color, the product made from these two different compositions yielded breads which tasted substantially the same.

To further investigate the effects of rehydrating dried yeast in chilled water, yeast was rehydrated in water maintained at approximately 0° C., as outlined above. The rehydrated yeast was then placed on a yeast growth medium, as is known in the art. The number of yeast cells which could be plated on such a medium decreased by 99% as compared to yeast which is rehydrated under conditions taught in the prior art. Similarly, 99% of the cells were unable to reduce methylene blue dye, indicating that the yeast were physiologically impaired or damaged. Accordingly, it is believed that rehydrating yeast in chilled water as described herein will tend to selectively lyse 95% or more of the yeast cells so hydrated.

EXAMPLE 2

The effect of incubation temperature upon dough compositions containing yeast rehydrated at 0° C. was measured and compared to the $CO_2$ evolution behavior of doughs containing yeast rehydrated at room temperature. One active dry yeast sample was rehydrated at approximately 0° C., while another sample was rehydrated at 23° C. The rehydration steps and dough mixing steps were substantially the same as outlined above in connection with Example 1, as were the ingredients added to the dough compositions. Once again, 50 gram samples of the desired dough composition were utilized in running carbon dioxide evolution determinations on the Risograph. The results of the Risograph testing are shown in FIGS. 3–8.

Figure 3:
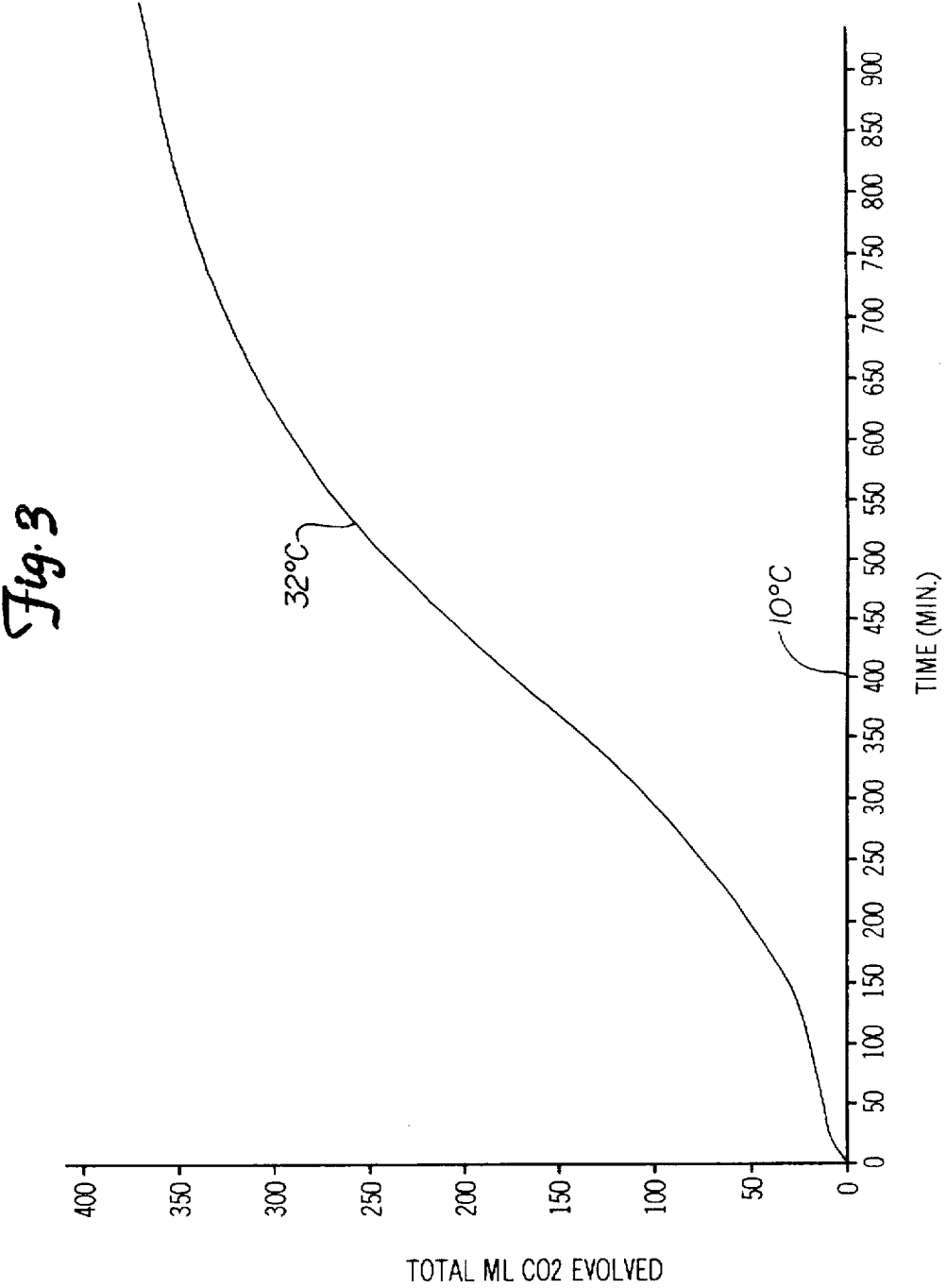
FIG. 3 is a graph showing the volume of carbon dioxide generated by yeast rehydrated at 0° C. in doughs heat treated at 10° C. and at 32° C.
Figure 4:
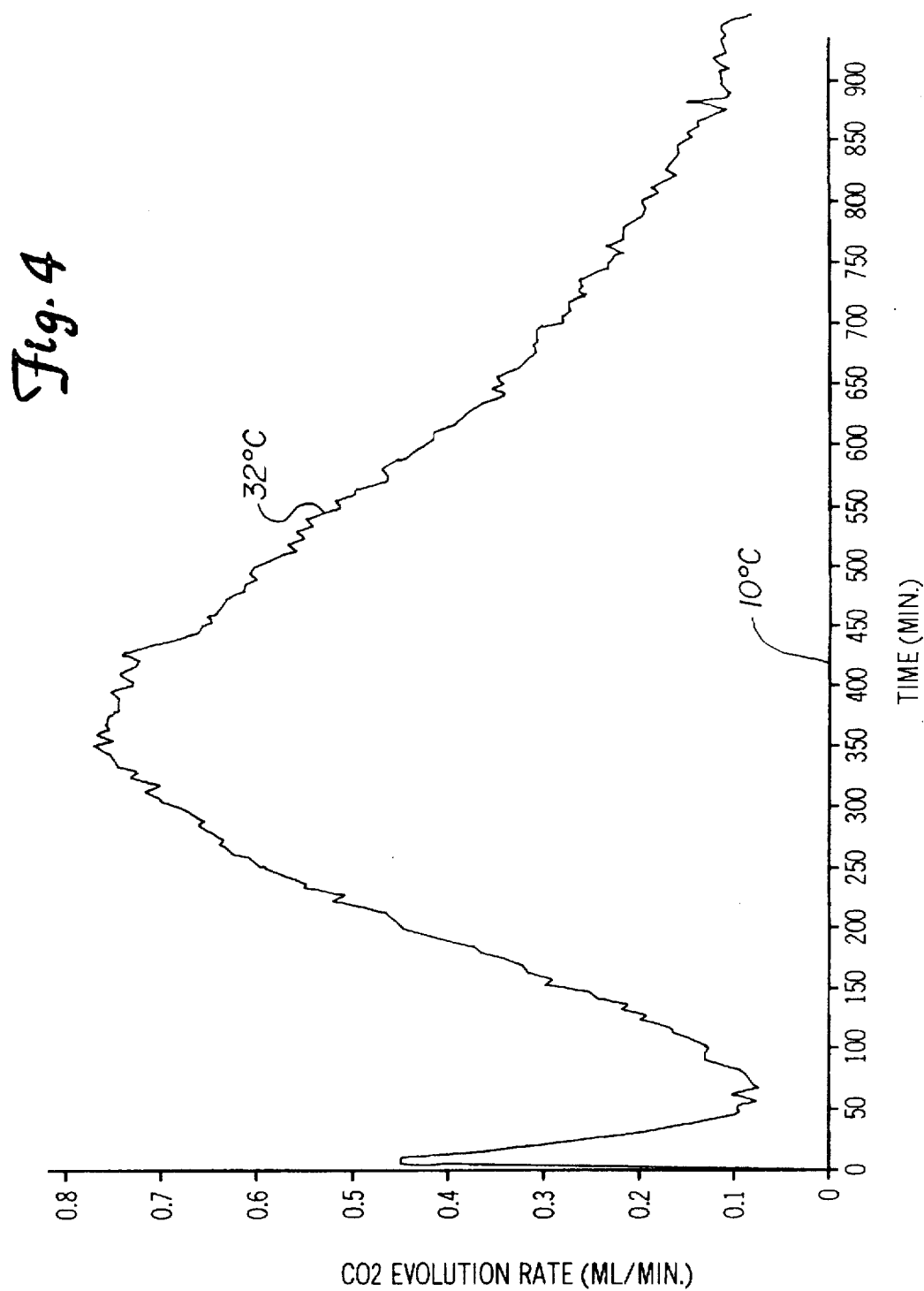
FIG. 4 is a graph showing the rate of carbon dioxide evolution of the two compositions shown in FIG. 3.
Figure 5:
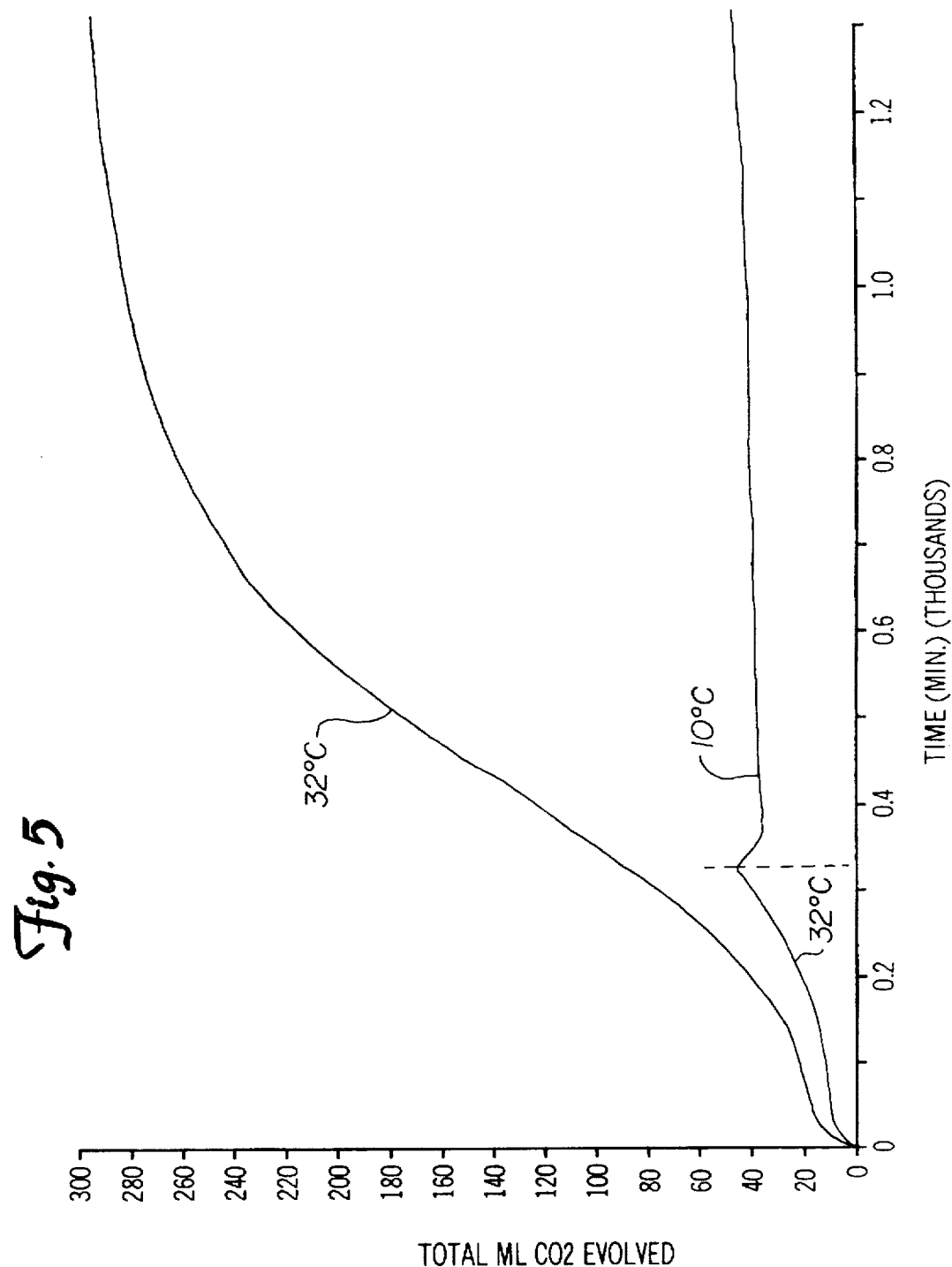
FIG. 5 is a graph showing the volume of carbon dioxide generated over time by doughs containing yeast rehydrated at 0° C. subjected to varying heat treatments.

In generating the graphs of FIGS. 3 and 4, two samples of dough containing 0° C.-rehydrated yeast were tested, with one sample being incubated at 32° C. while the other was incubated at 10° C. As is quite clear from the graph of FIG. 3, the dough composition incubated at 32° C. generated a significant amount of carbon dioxide (about 360 ml) over the course of the 17-hour Risograph test. The sample incubated at 10° C., though, did not generate any detectable amount of carbon dioxide. This is also borne out in FIG. 4, which shows the volumetric $CO_2$ evolution rate of the samples tested to generate FIG. 3. The line showing the evolution rate of the sample incubated at 32° C. substantially parallels the plot in FIG. 2 of the sample containing 0° C.-rehydrated yeast; the maximum evolution rate was somewhat greater in FIG. 4 (due to the fact that it was incubated at a slightly higher temperature), but the overall shape of the curve is substantially the same. The line along the bottom of this graph, however, indicates that there was no detectable carbon dioxide generated in the sample incubated at 10° C.

In order to more closely simulate the process used in most commercial operations, another pair of samples of the dough with 0° C.-rehydrated yeast were tested on the Risograph. As noted above, in most commercial operations, the dough will be proofed at an elevated temperature in order to sufficiently leaven the dough so that it is ready for baking. The dough may then be chilled for extended refrigerated storage. In generating FIGS. 5 and 6, one sample was incubated at 32° C. for the entire 21-hour time period, while another sample was incubated for approximately 5.85 hours at 32° C. and then chilled down to 10° C. and maintained at that temperature for the rest of the time period.

Once again, the plots of total $CO_2$ evolution and the rate of $CO_2$ evolution for the sample incubated at 32° C. parallel the general shapes of the corresponding plots shown in FIGS. 1–4. The sample incubated under conditions similar to commercial production environments showed a noticeable decrease in the detected level of carbon dioxide and carbon dioxide generation rate when the incubation temperature was decreased from 32° C. to 10° C. Although this may appear to be anomalous at first glance, it is likely due to a drop in pressure within the sealed Risograph in response to the decrease in temperature from 32° C. to 10° C. As is clear from FIG. 6, this caused the $CO_2$ evolution rate to drop precipitously to a negative value, but the plot stabilized over time to a point at which the $CO_2$ evolution rate oscillated between 0 and 0.03 ml per minute. This does result in a slightly positive slope in FIG. 5, indicating that some small amount of carbon dioxide continues to be generated even at 10° C.

However, as compared to the plot of the sample maintained at 32° C. throughout the test, it is quite clear that holding the dough at refrigeration temperatures, even after incubation at elevated temperatures, substantially arrests the evolution of carbon dioxide by the sample. As explained in connection with Example 3 below, it is believed that this continued generation of carbon dioxide should not be problematic in storing such doughs in commercially acceptable containers at refrigeration temperatures for extended periods of time.

Figure 8:
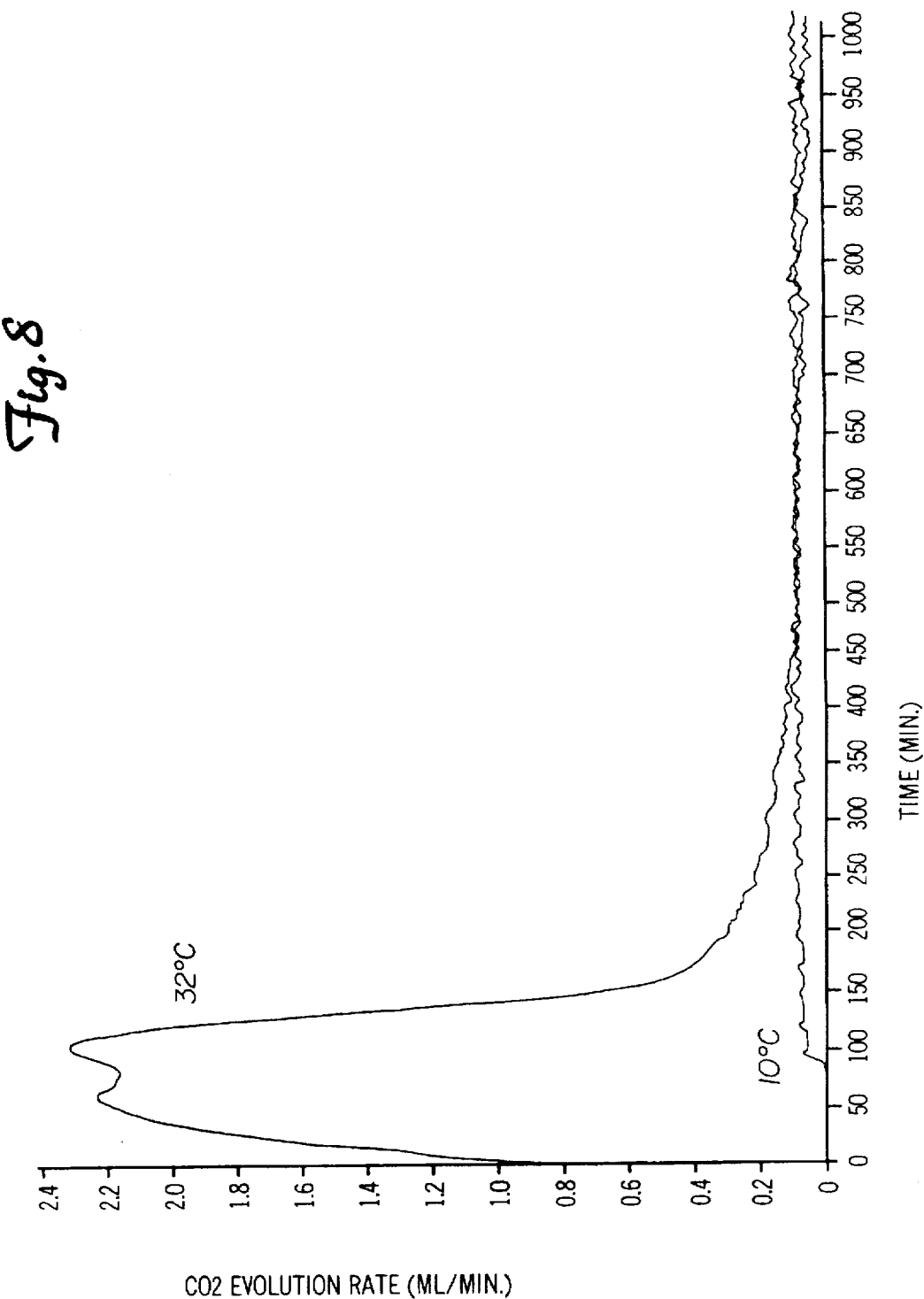
FIG. 8 shows the rate of carbon dioxide generation of the dough compositions shown in FIG. 7.

In order to provide a comparison of a dough composition of this invention with dough made in accordance with the prior art, a second batch of dough was made utilizing yeast rehydrated at 23° C., as noted above. In accordance with the procedure used in generating FIGS. 3 and 4, two 50-gram samples of this second dough composition were placed in a Risograph. One sample was incubated at 32° C., while the other was incubated at 10° C. By comparing FIGS. 3 and 4 to FIGS. 7 and 8, it is clear that a dough composition of the invention is much more suitable for extended storage at refrigerated in sealed containers. As noted above, the dough composition containing yeast rehydrated at 0° C. generated no detectable carbon dioxide. However, the sample of the dough containing 23° C.-rehydrated yeast began generating a significant amount of carbon dioxide after about 90 minutes of incubation at 10° C. As indicated in FIG. 8, this sample generated nearly 0.1 ml of carbon dioxide per minute even at 10° C. As further borne out by the slope of the line in FIG. 7 versus the slope of the 10° C. portion of the graph in FIG. 5, a dough composition according to the present invention generated significantly less carbon dioxide at refrigeration temperatures than a dough containing warm-rehydrated yeast even after the dough of the invention had been leavened at 32° C.

EXAMPLE 3

A dough composition containing yeast rehydrated at 0° C. was made in accordance with the procedure set forth above in relation to Example 1. After mixing the dough composition was sheeted to approximately ¼ inch thickness and cut into six 300 gram portions. Each portion was placed into a separate container and sealed. The containers were spirally wound composite cans, the likes of which are well known in the art. Such containers are generally designed to contain the dough under slight pressure, as explained above in connection with the process of proofing doughs. Such containers tend to rupture if the pressure therein exceeds approximately 40 psi. The six dough samples contained in the sealed containers were proofed at about 35° C. for approximately 7 to 8 hours until a can pressure of 5–10 psi was attained. The samples were then placed in a controlled temperature environment wherein the temperature was maintained between about 40° and about 45° F. (approximately 4.5°–7.2° C.) for a period of 90 days. This time period was chosen because 90 days is the approximate expected shelf life of most refrigerated dough products.

Figure 9:
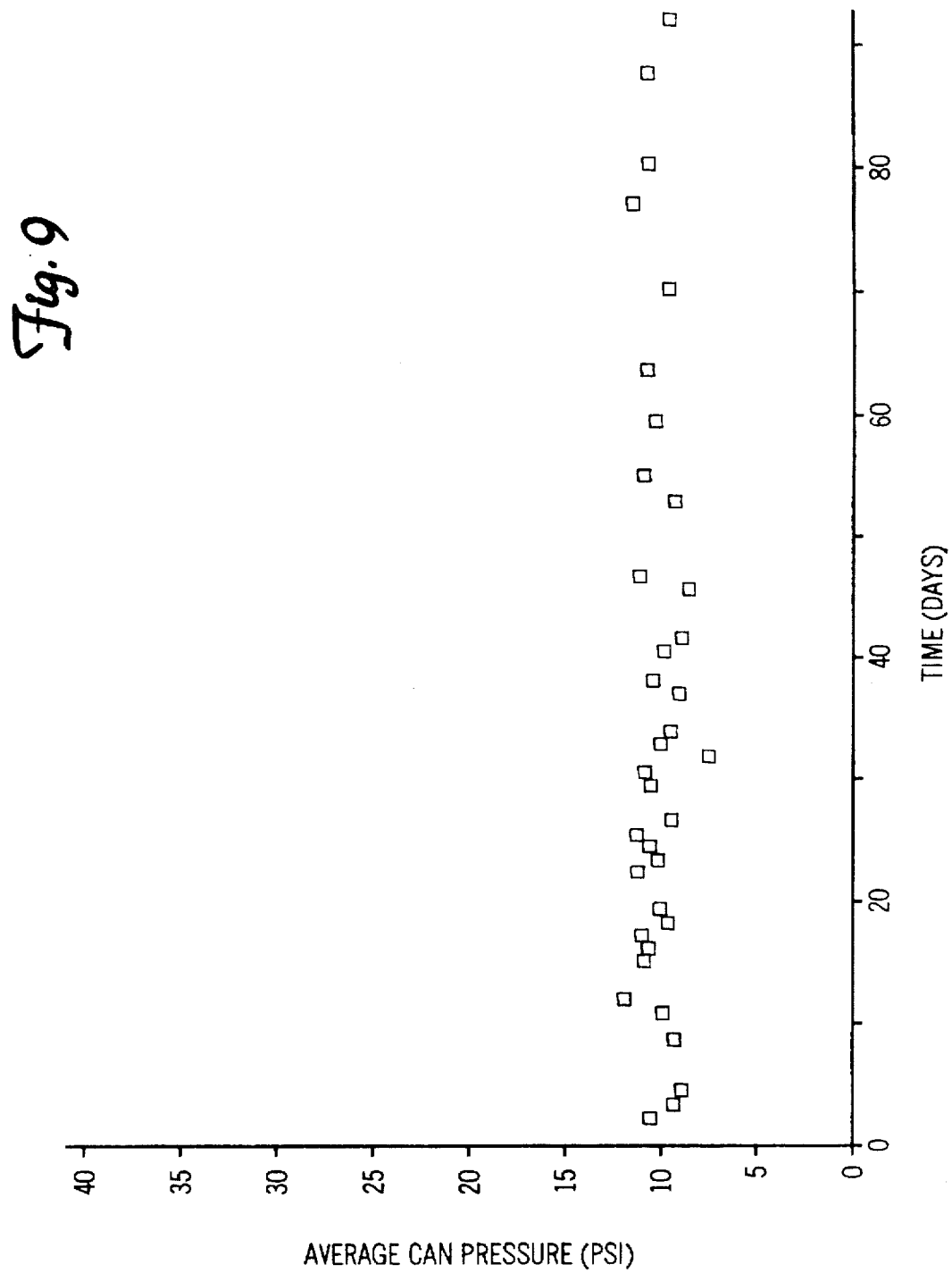
FIG. 9 is a graph showing the pressure within sealed containers containing dough compositions with yeast rehydrated at 0° C. over time at refrigeration temperatures.

The pressure within each container was measured using a Coyne pressure gauge, and the measurements so obtained for each of the six containers were averaged together to produce the data points on the graph of FIG. 9. As can be seen from that figure, the pressure in the containers remained relatively constant over the entire 90-day period of time at about 10±4 psi. Most importantly, the pressure within these cans remained well below the 40 psi limit on the pressure which these containers can withstand. Thus, yeast-leavened dough according to the instant invention can be stored in common spirally-wound composite cans at refrigeration temperatures for at least the 90-day period expected shelf life of commercial refrigerated doughs.

EXAMPLE 4

As explained above, it is generally preferred that the yeast obtained by the cold rehydration process taught herein have about 97–99% of the yeast cells selectively lysed; the remaining 1–3% of the yeast desirably remains viable. In order to compare the results obtained in Example 3 above with a similar sample containing an analogous weight percent of viable yeast cells, a second dough composition was prepared. The dough composition utilized in this second test is substantially the same as that utilized in Example 3, only the concentration of yeast was changed. The yeast utilized in this test was rehydrated at 23° C. as opposed to about 0° C., and the yeast concentration was reduced to about 0.015 wt. %. This yeast concentration presents the same weight percent of fully viable yeast cells that a sample according to the present invention would provide if approximately 98.5% of the cells therein were selectively lysed.

Figure 10:
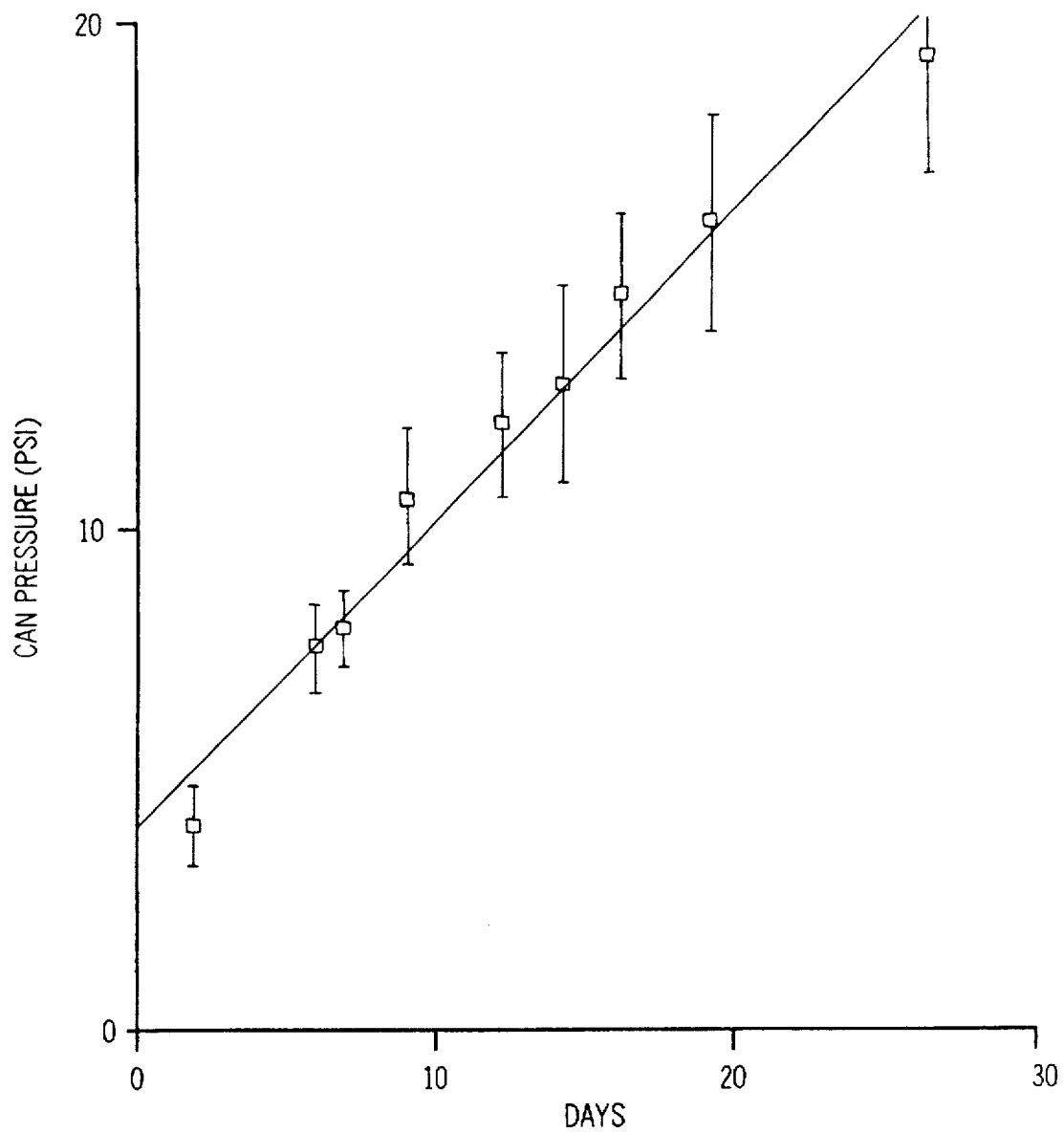
FIG. 10 is a graph similar to FIG. 9, but showing data generated using dough leavened with a very small concentration of yeast (0.015%) rehydrated at 23° C.

Six samples of the resulting dough composition were each placed into individual, sealed containers and maintained at refrigeration temperatures in substantially the same manner as set forth above with regard to Example 3. The resulting pressures within these containers are shown in FIG. 10, with each data point being representing an average for the four samples and a pair of bars indicating the standard deviation of each average. Although the data shown in FIG. 10 were collected over a shorter period of time, it is quite clear that the pressure within the containers increased quite steadily. Regression analysis of the data shown in FIG. 10 indicates that the pressure within the containers would exceed the critical 40 psi level after only 57–58 days of storage at refrigeration temperatures. As this falls well short of the 90-day expected shelf life of such products, it is clear that even reducing the concentration of warm-rehydrated yeast in a dough is insufficient to provide a suitable dough product for refrigerated storage.

By comparing the data shown in FIG. 10 with that shown in FIG. 9, it is clear that the rehydration process utilized in the present invention produces a yeast which differs rather markedly from yeast rehydrated according to commonly accepted practice. In particular, yeast according to the present invention appears to be sensitized to cold such that when a dough composition made in accordance with the invention is held at refrigeration temperatures, the yeast therein becomes inactive, i.e., substantially ceases production of carbon dioxide. On the other hand, even with a comparable concentration of viable yeast cells, dough compositions containing yeast rehydrated according to the prior art are simply unsuited for extended refrigerated storage because $CO_2$ continues to evolve even at refrigeration temperatures.

EXAMPLE 5

In order to test the efficacy of the substrate limiting embodiment of the present invention as a means of providing a refrigeratable yeast-leavened dough composition, water and a MAL– yeast were slurried together to produce a total combined weight of approximately 194.69 grams. The slurry contained 189.89 grams of water and 4.8 grams of the yeast. The yeast used in making the slurry was a MAL– strain of yeast which was obtained in a paste form. The paste was mixed with water at room temperature (approximately 23° C.) and allowed to sit at room temperature for about 10–15 minutes.

To this slurry was added 261.74 grams of flour, 18.77 grams of the gluten pre-blend described in connection with Example 1, 3.60 grams of salt and 1.20 grams of dextrose. The resulting dough composition therefore contained 54.53 wt. % flour, 3.91 wt. % gluten pre-blend, 0.75 wt. % salt, and 0.25 wt. % dextrose, with a final concentration of 1.00 wt. % MAL– yeast. The dough composition was mixed in a, farinograph mixing bowl at 60 rpm for 4.5 minutes. Immediately after mixing, a 50-gram sample of the dough composition was placed into the Risograph testing machine used in connection with Examples 1 and 2 above.

Figure 11:
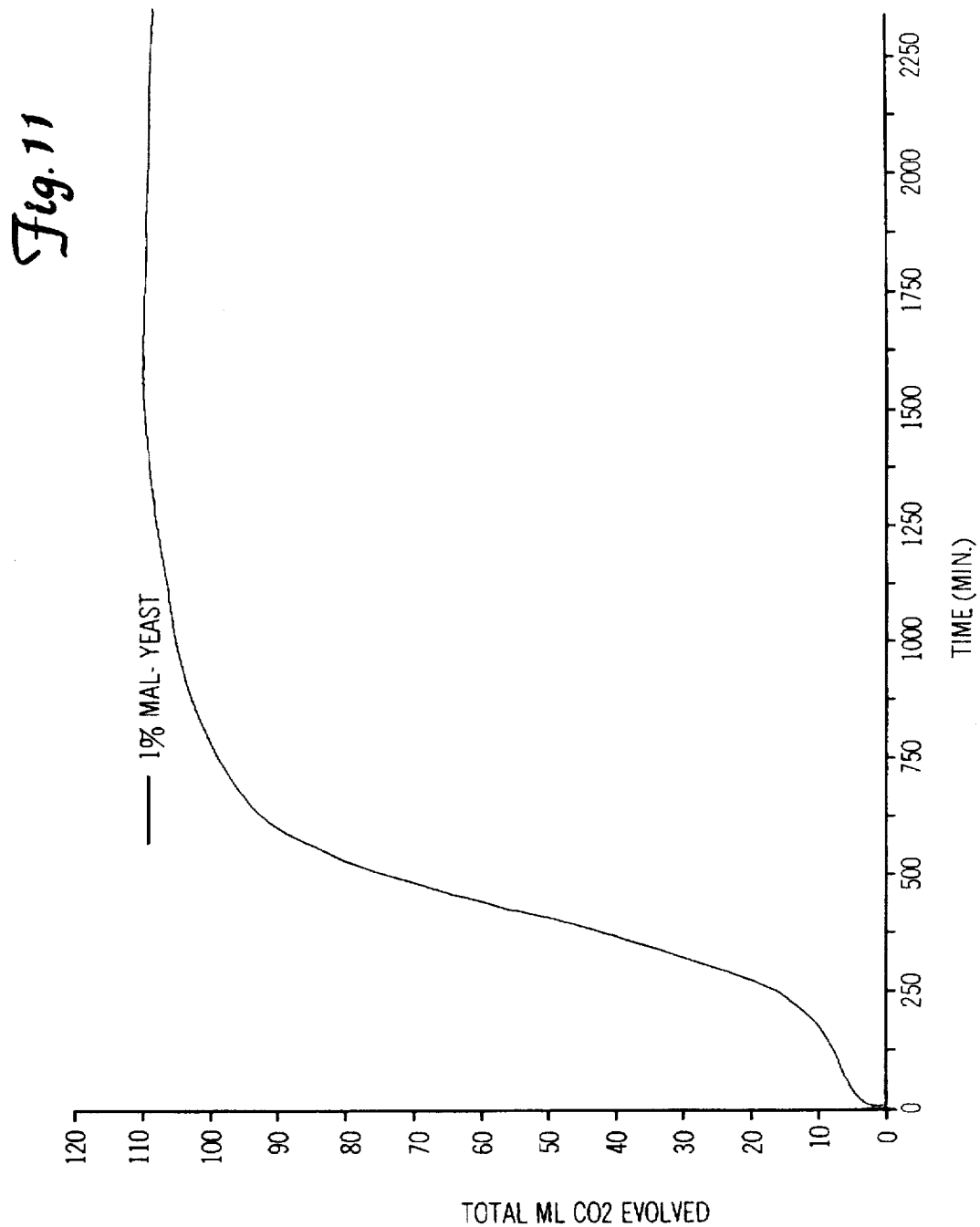
FIG. 11 is a graph showing the volume of carbon dioxide generated by MAL– yeast in a dough composition heat treated at 32° C.
Figure 12:
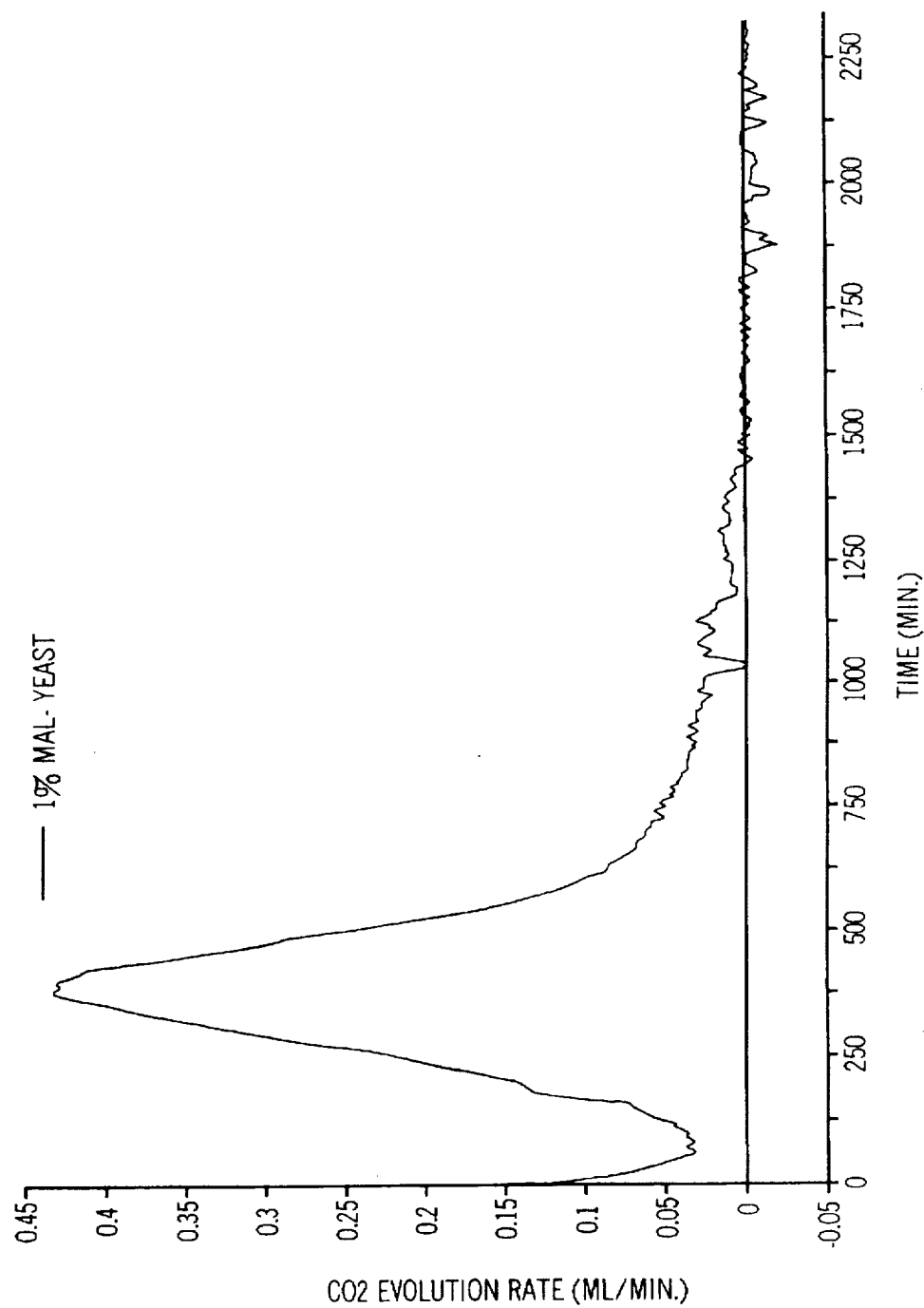
FIG. 12 shows the rate of carbon dioxide evolution for the dough shown in FIG. 11.

FIGS. 11 and 12 shown the data collected in the Risograph for the sample. Of particular interest, it is clear that the dough effectively ceased producing carbon dioxide after about 1500 minutes at 32° C.

The total volume of carbon dioxide generated has some interesting implications on a quantitative level. As noted above, approximately 100 ml of carbon dioxide per 100 grams of dough is generally considered sufficient to leaven dough for baking. As also explained above, the size of the sample placed in the Risograph in the present example was 50 grams. As best seen in FIG. 11, the 50-gram sample of the dough generated only slightly more than 100 ml of carbon dioxide. Accordingly, the results of this test would indicate that a concentration of approximately 1 wt. % MAL– yeast in a dough composition containing about 0.25 wt. % dextrose would yield a dough composition which, when allowed to ferment in the dough for a period of time commensurate with the evolution of approximately one-half of the total amount of $CO_2$ evolved, is ideally suited for extended storage because subsequent carbon dioxide generation in the sealed container substantially ceases after the ideal volume of carbon dioxide has been generated.

EXAMPLE 6

In order to test the temperature sensitivity of a dough containing lts yeast, a dough composition containing such a yeast was made and the volume of carbon dioxide generated by samples subjected to varying heat treatment profiles was measured. In making the dough, 14 g (2 wt. %) of lts yeast was added to 243.74 g (34.83 wt. %) of water. The yeast used in this experiment was a low temperature sensitive mutant strain of S. cerevisiae designated as XA7734-B; this yeast was of the genotype lts3 leu1 cyh2 met13 aro2 lys5 trp5. This yeast is available to the public from the Yeast Genetic Stock Center at the Donner Laboratory in the Department of Molecular and Cell Biology at the University of California, Berkeley (YGSC); in the 7th Edition of the catalog of the YGSC, dated Mar. 15, 1991, this strain of yeast was listed under stock no. XA7734-B. This "lts3" yeast was deposited with the American Type Culture Collection, of 12301 Parklawn Drive, Rockville, Md. (ATCC), on 31 Jan. 1992, under number ATCC 74126. The water to which the yeast was added contained 30 mg/l of the following amino acids: leu, met, phe, try, trp, and lys. The pH of the water was adjusted to approximately 6.91 with dilute sodium hydroxide. The yeast and water were slurried together and held at approximately 23° C.

The resultant yeast slurry was poured into a table-top Hobart mixing bowl and the following dry ingredients were also added: 402.71 g (57.53 wt. %) of wheat flour, 27.30 g (3.90 wt. %) of wheat gluten, 7.0 g (1.0 wt. %) of dextrose, and 5.25 g (0.75 wt. %) of salt. The ingredients were then mixed relatively slowly with a dough hook for about 30 seconds, followed by a more rapid rate of mixing for about 4 minutes.

After mixing was completed, six 50-gram samples of the dough were placed into Risograph sample jars. After being attached to the Risograph, four of the jars were placed into a water bath in the Risograph set at 32° C. while the other two samples were placed into a 10° C. external water bath. After approximately 24 hours, two of these samples placed in the 32° C. water bath were transferred to the external 10° C. water bath.

Figure 13:
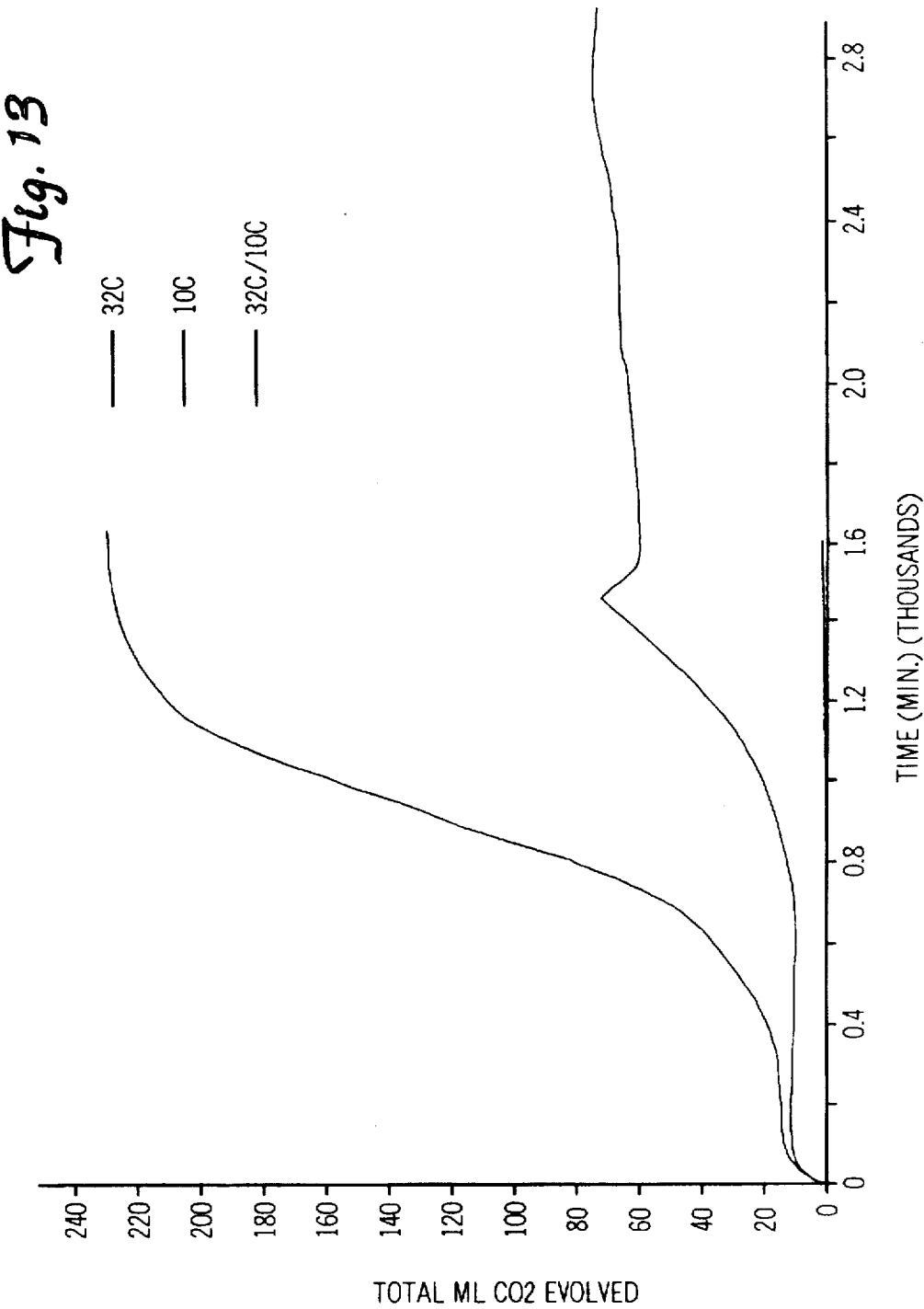
FIG. 13 is a graph showing the volume of carbon dioxide generated by a dough composition containing lts3 yeast and incubated at 32° C., 10° C., and at 32° C. then 10° C.
Figure 14:
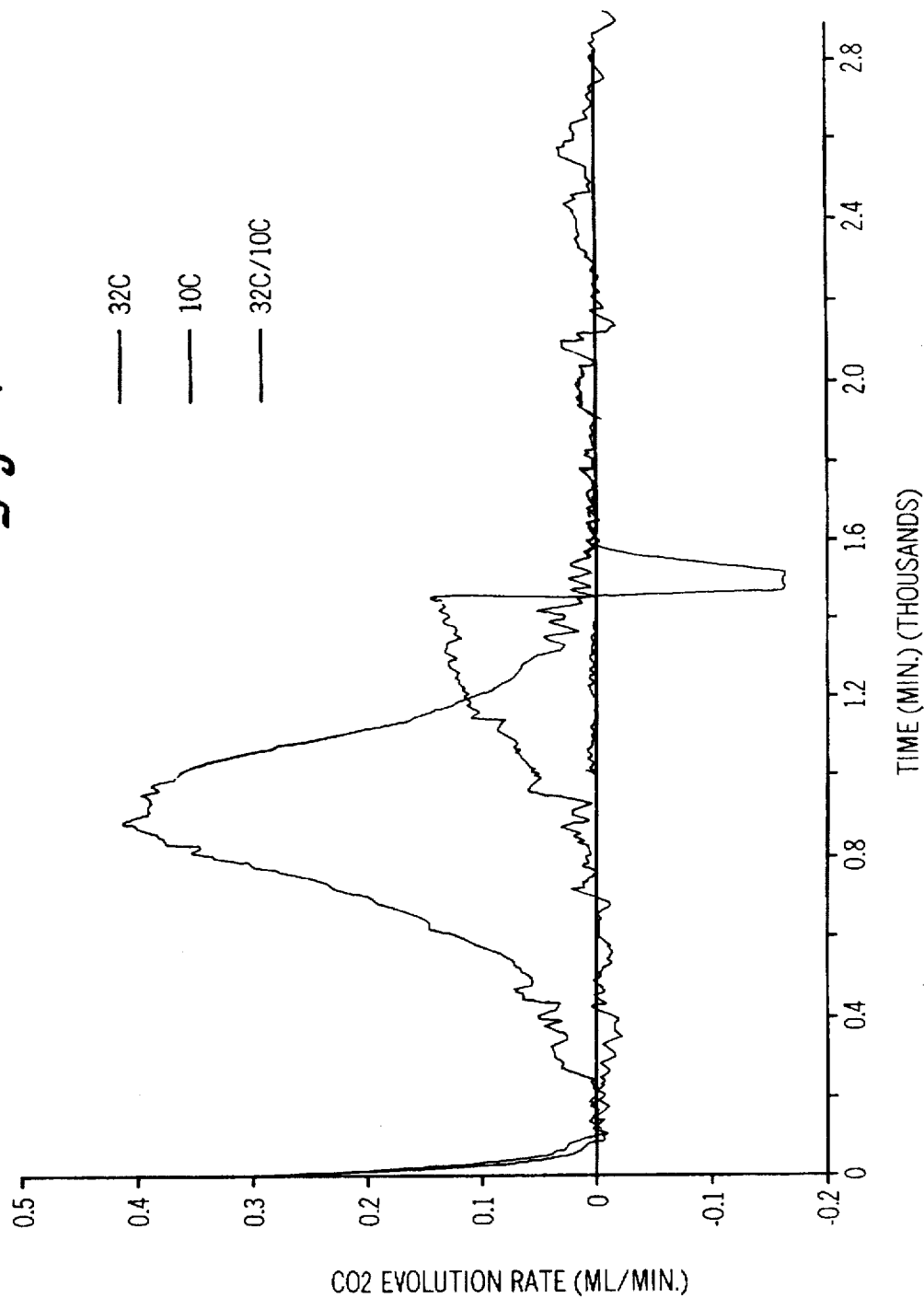
FIG. 14 shows the rate of carbon dioxide generation of the dough compositions shown in FIG. 13.

FIGS. 13 and 14 show the results of this Risograph testing. FIG. 13 shows the total volume of carbon dioxide generated by each pair of dough samples as a function of time. FIG. 14 shows the rate of carbon dioxide generation of the samples over time. The samples held at 32° C. followed a typical $CO_2$ evolution profile for a yeast-leavened dough composition. Such profiles typically include an initial lag phase followed by an active carbon dioxide evolution phase, which leads into a decline phase. This sample generated a total of approximately 225 ml of carbon dioxide over the course of the testing.

However, the total amount of carbon dioxide generated by the samples held at 10° C. generated only a negligible amount of carbon dioxide, on the order of 1–2 ml. It should be noted that the mutant expression temperature for this strain of yeast is believed to be about 10° C. Thus, there was clearly a marked difference in the behavior of this dough sample at these two temperatures.

The $CO_2$ generation profile of the samples treated initially at 32° C. then held at 10° C. are also shown in FIGS. 13 and 14. As shown in those figures, the sample relatively vigorously generated carbon dioxide when held at 32° C. When the samples were moved from the warm water bath to the 10° C. water bath, though, there was an initial drop in the volume of $CO_2$ detected by the Risograph. This is particularly borne out in FIG. 14, which shows a negative carbon dioxide evolution rate once the sample is transferred. This is most likely due to the change in the temperature of the water bath, which would result in a drop in the pressure within the container. During incubation at 10° C., this sample experienced an extended period of minimal carbon dioxide production, followed by a 3-hour period at the end of the test with no measurable change in carbon dioxide volume.

This last temperature profile is analogous to that which would be utilized during standard commercial processing. As noted above, such commercial processing would include an initial proofing stage at an elevated temperature wherein carbon dioxide is generated, followed by storage at refrigeration temperatures, e.g., 10° C. As can be seen in FIGS. 13 and 14, this temperature profile would appear to work quite well for such commercial products. A sufficient volume of carbon dioxide was generated at elevated temperatures to proof the dough, yet carbon dioxide generation substantially ceased after stabilizing when held at 10° C. This would indicate that the sample could be held at 10° C. for extended periods of time without generating sufficient volumes of carbon dioxide to cause any storage difficulties.

EXAMPLE 7

Two dough formulas were prepared using lts1 or lts2 strains of mutant S. cerevisiae yeast. These samples were prepared in much the same manner as the lts3 dough sample set forth in Example 6. (It is to be noted that the numeral following the designation "lts" is intended to refer to a specific genetic locus which affects low-temperature-sensitive growth of the yeast.) The lts1 yeast mutant strain was designated as XA6-94C, of the genotype a lts1 leu1 trp5 lys2 can1; the lts2 yeast mutant strain was designated as XA6-94B and was of the genotype a lts2. Both of these lts mutant strains of yeast are publicly available from the Yeast Genetic Stock Center at the University of California at Berkeley, noted above. The catalog numbers for the lts1 and lts2 yeasts in the 7th Edition of the YGSC catalog were XA6-94C and XA6-94B, respectively. These yeasts were deposited with the ATCC on 31 Jan. 1992 under numbers ATCC 74124 and ATCC 74125, respectively.

The lts1 dough formula was prepared as follows: 12.80 g (1.65 wt. %) of the lts1 yeast was added to 271.67 g (34.95 wt. %) of water. This yeast/water slurry was added to 448.73 g (57.73 wt. %) of ground wheat flour, 30.42 g (3.91 wt. %) of wheat gluten, 7.80 g (1.00 wt. %) of dextrose, and 5.85 g (0.75 wt. %) of salt. The lts2 dough composition included 9.50 g (2.00 wt. %) of the lts2 yeast, 165.44 g (34.83 wt. %) of water, 273.27 g (57.53 wt. %) of wheat flour, 18.53 g (3.90 wt. %) of wheat gluten, 4.75 g (1.00 wt. %) of dextrose, and 3.56 g (0.75 wt. %) of salt.

These dough compositions were mixed in substantially the same manner as set forth in Example 1. Six 50-g samples of each of these resultant doughs were placed into Risograph sample jars. After being attached to the Risograph, four of the jars were placed into the Risograph water bath held at 32° C. while the remaining two samples were placed into a 10° C. external water bath. After approximately 24 hours, two of the samples held in the 32° C. water bath were transferred to the external 10° C. water bath. This heat treatment regimen is substantially identical to that set forth in Example 6.

Figure 15:
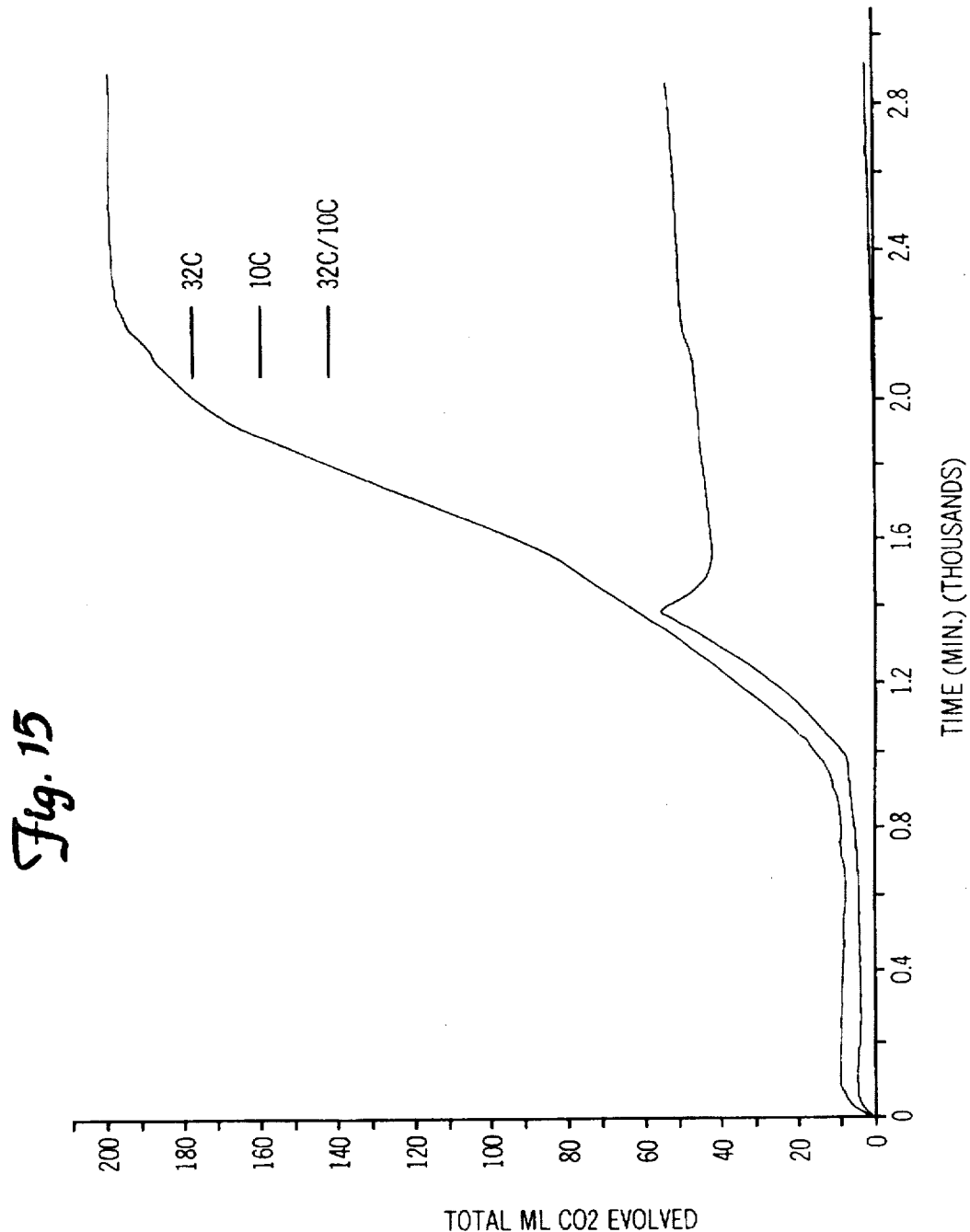
FIG. 15 is a graph showing the volume of carbon dioxide generated by a dough composition containing lts2 yeast and incubated at 32° C., 10° C., and at 32° C. then 10° C.
Figure 16:
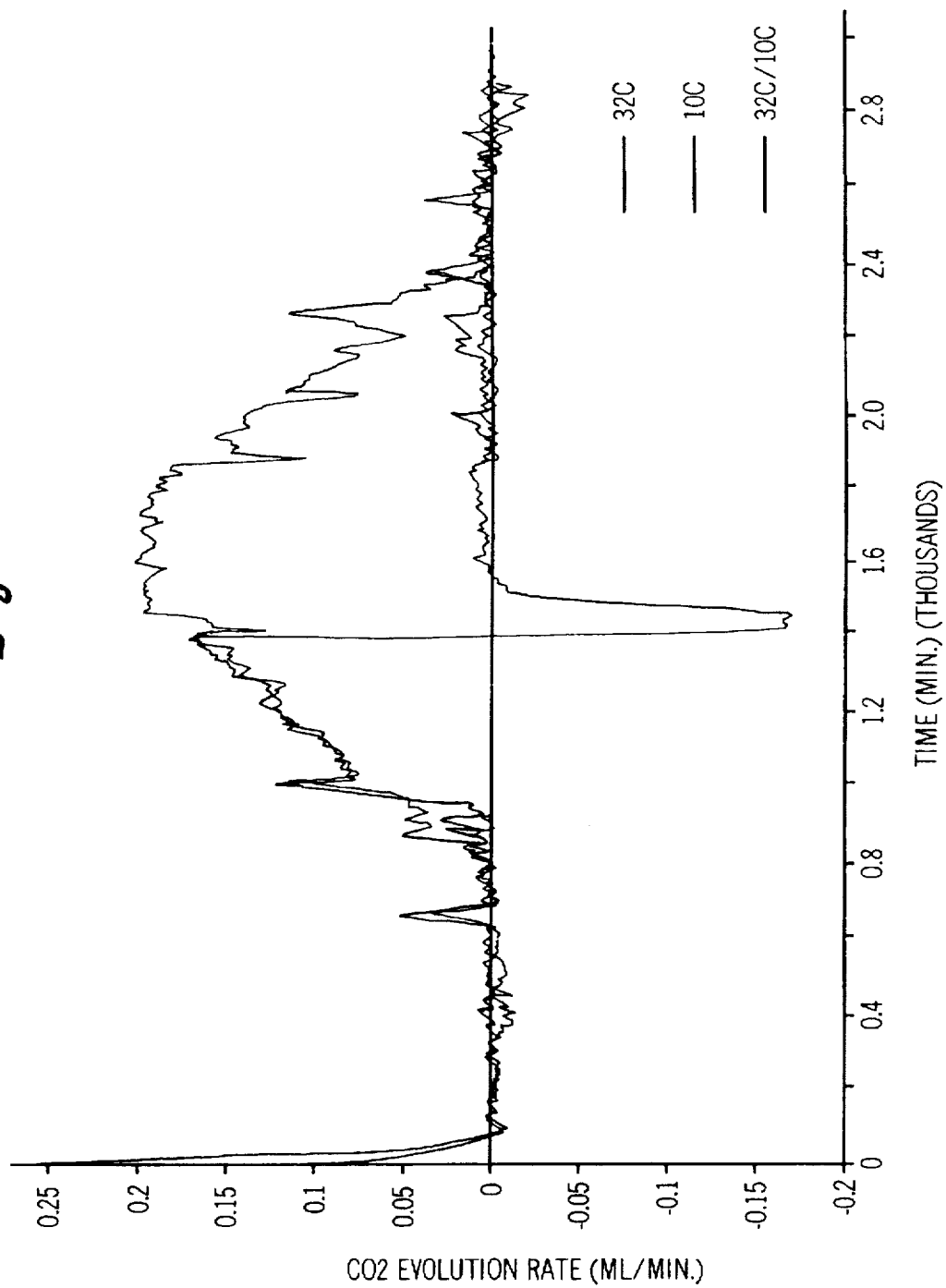
FIG. 16 shows the rate of carbon dioxide generation of the dough compositions shown in FIG. 15.

FIGS. 15 and 16 show the volume of carbon dioxide generated over time and the rate of carbon dioxide generation over time, respectively, for the lts2 dough samples. Similarly, FIGS. 17 and 18 show the volume of carbon dioxide generated over time and the rate of carbon dioxide generation over time, respectively, for the lts1 yeast composition.

Referring first to FIGS. 15 and 16, the gas evolution profiles for the lts2 dough would appear to be substantially similar to those set forth in FIGS. 13 and 14 for the lts3 dough composition. In particular, the sample held at 32° C. followed a typical carbon dioxide evolution pattern, while the sample held throughout the length of the experiment at 10° C. generated virtually no carbon dioxide during the course of the experiment. Also as in Example 6, the sample which was switched to 10° C. generated carbon dioxide when in the warm water bath, and showed an initial drop in pressure when switched to the 10° C. water bath. This sample showed an extended period of rather slow carbon dioxide production, not unlike the lts3 samples of Example 6. Whereas the lts3 dough compositions substantially ceased carbon dioxide production by the end of the experiment, though, carbon dioxide production in the lts2 dough in this example did not appear to fully level off by the end of the test. It is not certain whether this sample would have ceased producing carbon dioxide if the experiment were continued. Nonetheless, the rate of carbon dioxide production by this sample was minimal, being on the order of about 0.01 ml of carbon dioxide per minute.

Figure 6:
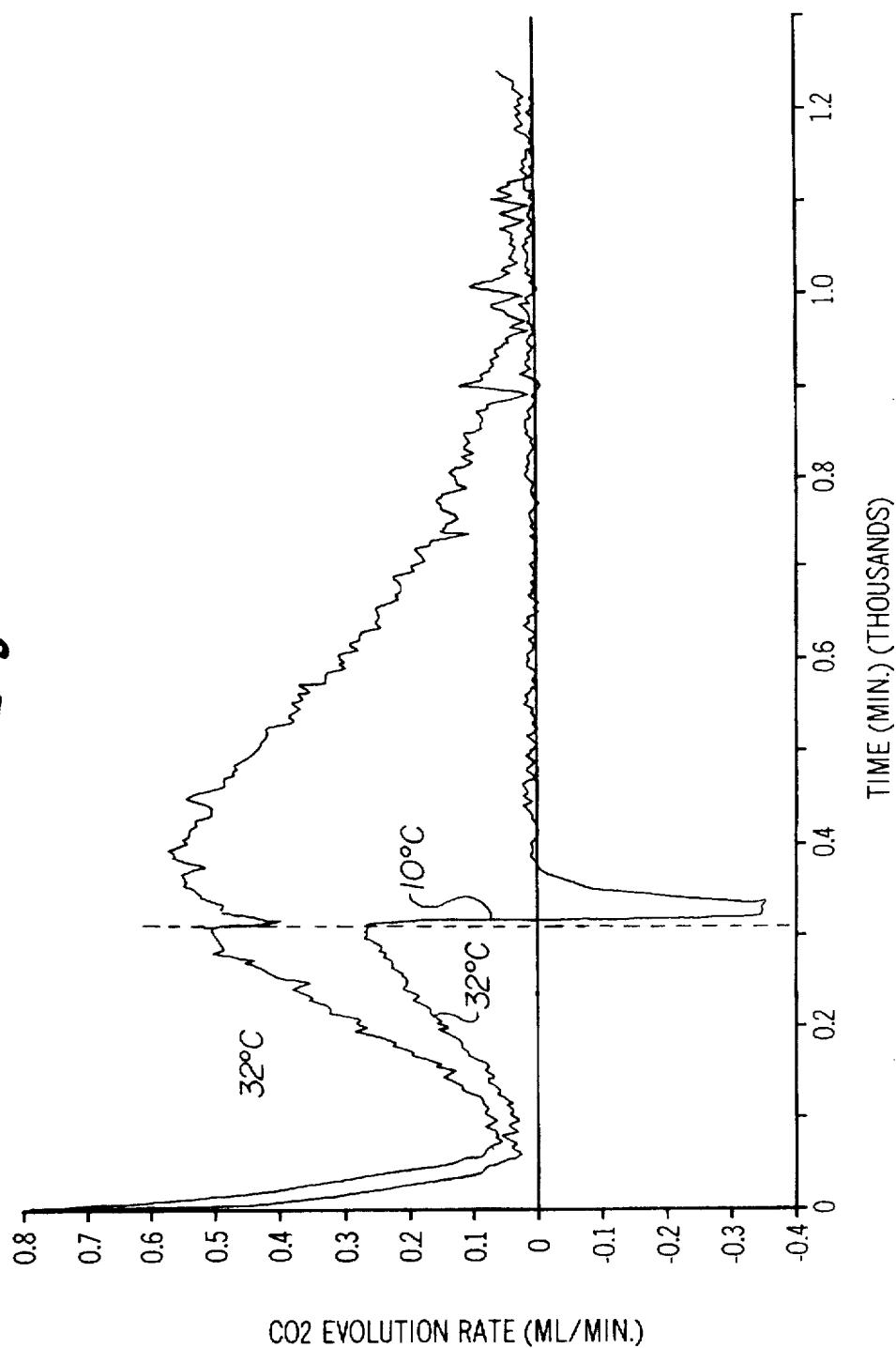
FIG. 6 shows the rate of carbon dioxide evolution for the doughs shown in FIG. 5.
Figure 7:
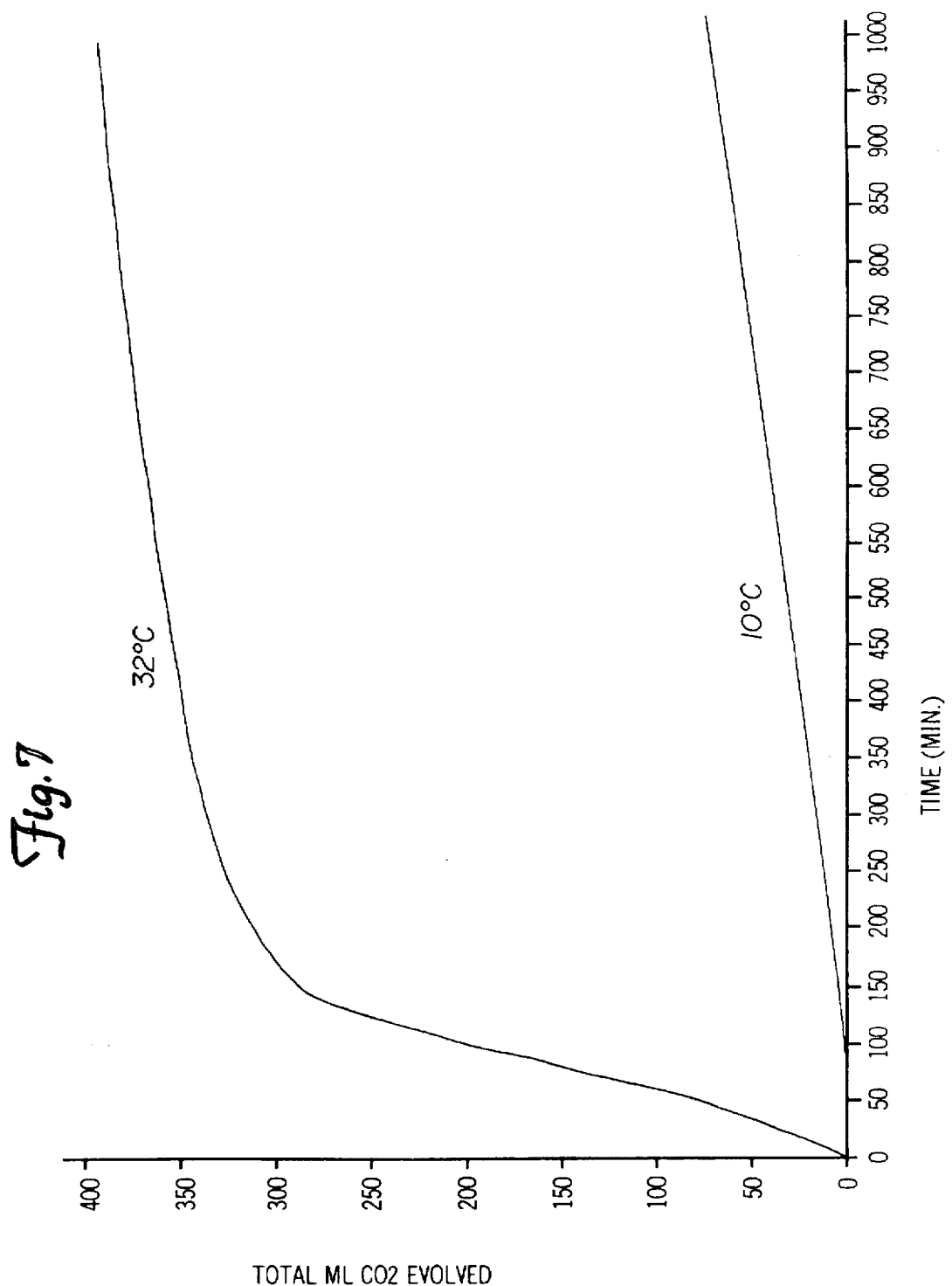
FIG. 7 is a graph showing the total volume of carbon dioxide generated by dough compositions containing yeast rehydrated at 23° C. and incubated at 32° C. and 10° C.
Figure 17:
FIG. 17 is a graph showing the volume of carbon dioxide generated by a dough composition containing lts1 yeast and incubated at 32° C., 10° C., and at 32° C. then 10° C.
Figure 18:
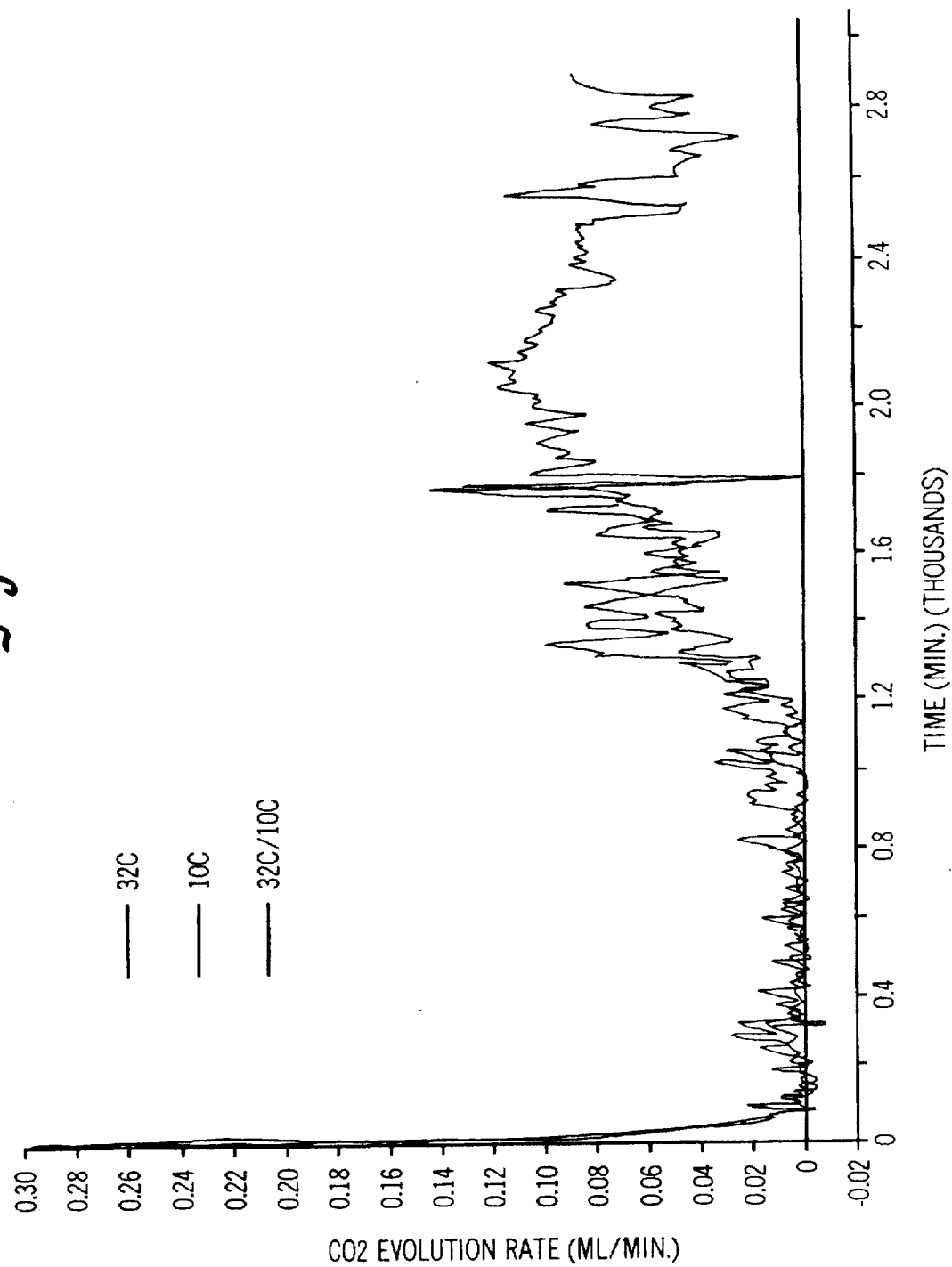
FIG. 18 shows the rate of carbon dioxide generation of the dough compositions shown in FIG. 17.

The results of the testing on the lts1 dough, shown in FIGS. 17 and 18, are similar to the results for the lts2 and lts3 doughs. Although the lag time in this dough seemed to be longer than in the previous tests, the 32° C. samples generated a significant volume of carbon dioxide while the samples held at 10° C. evolved no detectable carbon dioxide. Once again, the other pair of samples generated significant volumes of carbon dioxide at 32° C., but substantially ceased production of carbon dioxide when switched to the 10° C. water bath. As shown in FIG. 6, the carbon dioxide evolution rate immediately dropped to 0 ml per minute when the sample was switched to the 10° C. water bath. As noted above, there is a significant pressure drop on this change in temperature, which can lead to readings which would appear to indicate a negative carbon dioxide evolution rate. The results shown in FIGS. 17 and 18 for the 32° C./10° C. sample are believed to be attributable to the same pressure drop. It is speculated that when the sample was placed into the 10° C. water bath the head space of gas in the sample jar condensed, forming a relative vacuum. The yeast in this sample, though, never generated sufficient carbon dioxide to compensate for this vacuum because carbon dioxide production essentially ceased. Accordingly, the Risograph recorded 0 ml gas evolved for the remainder of the experiment.

The results of these tests on the lts1 and lts2 dough compositions confirm the results noted with the lts3 yeast. In particular, the doughs made with the lts yeasts exhibited essentially normal carbon dioxide evolution profiles at elevated temperatures, yet substantially stopped producing carbon dioxide when held at refrigeration temperatures. The samples initially held at 32° C. and then switched to 10° C. indicate that a dough composition of the invention can be used in a commercial processing scenario. In particular, they can be leavened at an elevated temperature, then held at refrigerated temperatures to substantially cease production of carbon dioxide for extended refrigerated storage.

EXAMPLE 8

In order to eliminate interference in the results from bacterial growth and to minimize the extended lag phase, an lts1 dose sample was prepared in a manner similar to that set forth above for example 7. However, an antibiotic was added to the water in order to inhibit bacterial growth and the yeast was incubated in a dextrose solution prior to being mixed with the rest of the dough components.

The actual dough composition included 348.3 g (34.71 wt. %) of water, to which had been added 50.3 miligrams of chloramphenicol, an antibiotic adapted to inhibit the growth of bacteria, 575.30 g (57.24 wt. %) of flour, 39.0 grams (3.88 wt. %) of wheat gluten, 10.0 grams (0.99 wt. %) of dextrose, 7.50 grams (0.75 wt. %) of salt, and 25 grams (2.48 wt. %) of yeast. The water containing the chloramphenicol was mixed with the dextrose and yeast and incubated at 32° C. for approximately two hours to initiate yeast fermentation. This yeast slurry was then combined with the additional ingredients in a tabletop Hobart mixer equipped with a dough hook. The ingredients were then mixed relatively slowly for about 30 seconds, followed by a more rapid rate of mixing for about 4 minutes.

Six 50-gram samples of the resulting dough were placed into Risograph sample draws and subject to substantially the same heat treatment set forth in Examples 6 and 7. However, after approximately 1,300 minutes of incubation, the sample initially held at 32° C. and what was removed and the samples in the 10° C. water bath were moved to the 32° C. waterbath.

Figure 19:
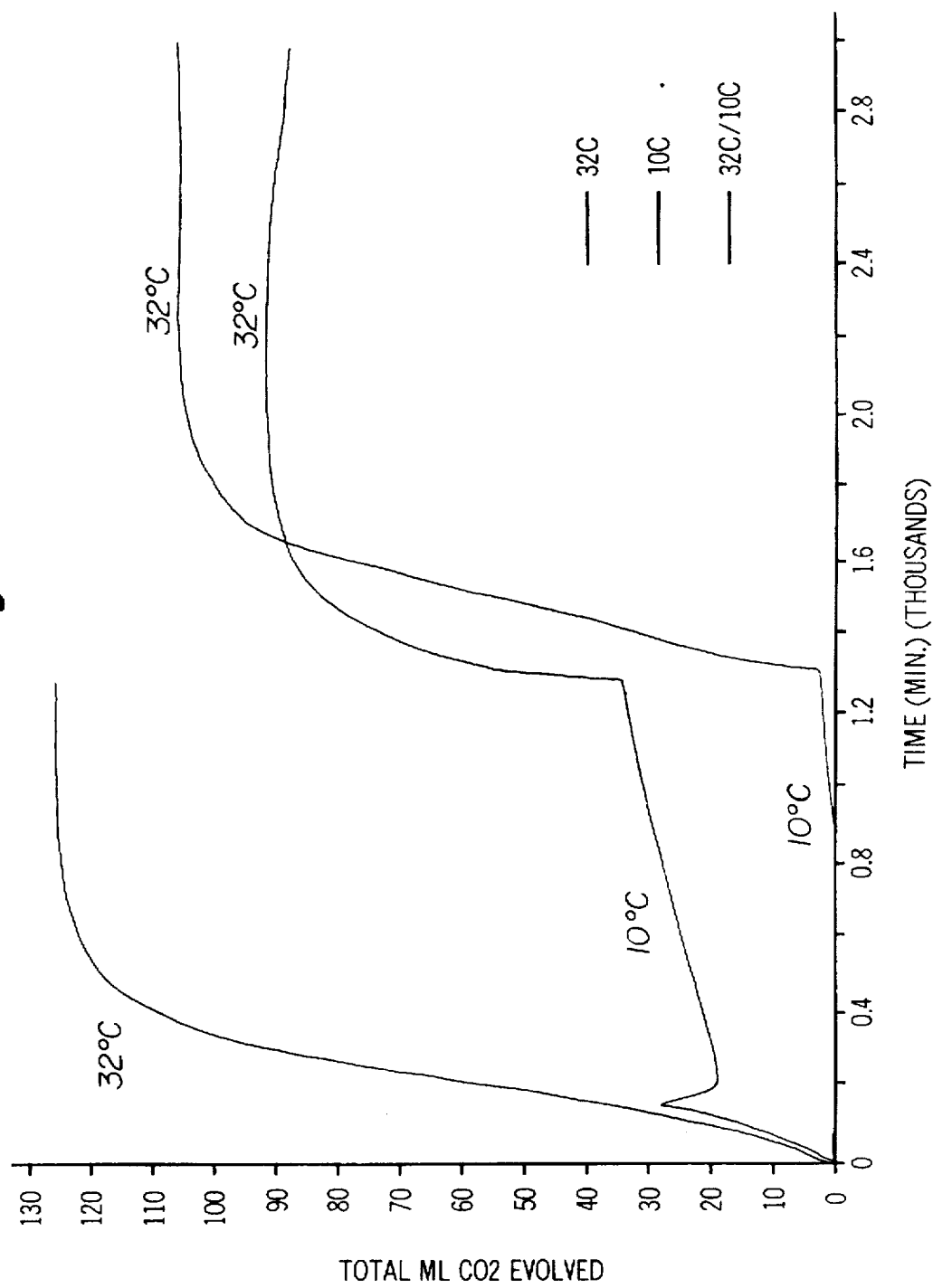
FIG. 19 is a graph showing the volume of carbon dioxide generated by a dough composition containing lts1 yeast which has been treated with an antibiotic and incubated at 32° C., 10° C., and at 32° C. then 10° C.
Figure 20:
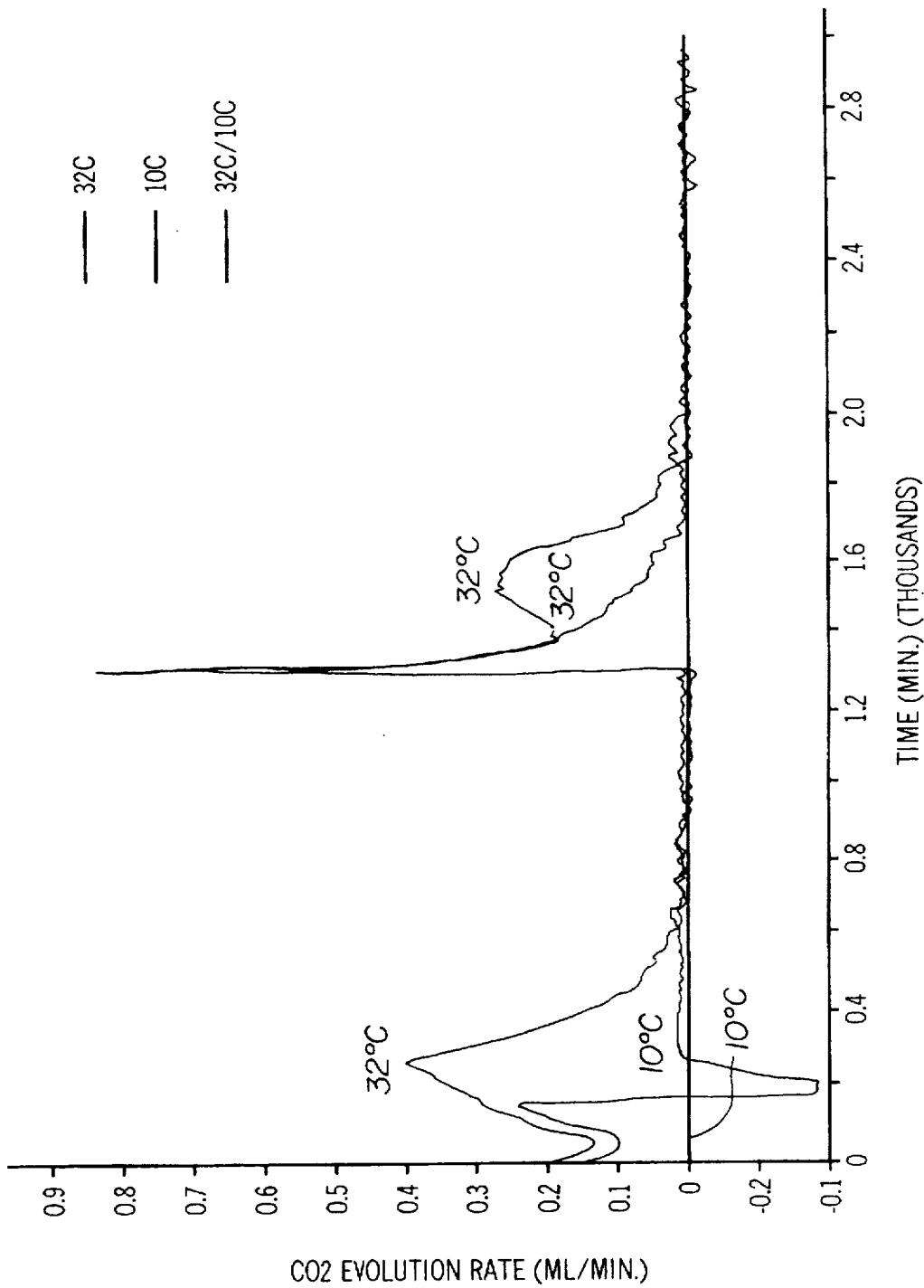
FIG. 20 shows the rate of carbon dioxide generation of the dough composition in FIG. 17.

The results of this experiment are shown in FIGS. 19 and 20. As shown in FIG. 19, the results are generally analogous to those shown in FIG. 17, except the prolonged lag phase shown in FIG. 17 was not detected with the present test. This was believed to be due to the fact that the yeast had been incubated with the fermentable substrate prior to addition of the rest of the ingredients to form the dough. FIGS. 19 and 20 also clearly show a marked increase in carbon dioxide evolution when the sample is transferred from the 10° C. environment to the 32° C. environment. This indicates that the yeast remains viable and is capable of producing carbon dioxide even after extended storage at refrigeration temperatures.

Similar tests were conducted with five additional strains of yeast—lts4, lts5, lts6, lts7 and lts8. Each of these yeast strains are available to the public from the YGSC at the University of California, Berkeley. In the seventh addition of the catalog of the YGSC, dated Mar. 15, 1991, these strains were listed under stock numbers XA99-13C, XA98-3D, XA88-3A, XA89-2A, and XA33-5A, respectively. Additionally, each of these yeasts were deposited with the ATCC on 31 Jan. 1992, under numbers ATCC 74127, ATCC 74128, ATCC 74129, ATCC 74130, and ATCC 74131, respectively.

Analogous results were obtained for each of those samples. More particularly, each of the samples showed rather vigorous production of carbon dioxide at elevated temperatures, but little or substantially no carbon dioxide production at refrigeration temperatures. Each of these yeasts also indicated that they remain viable after extended refrigerated storage by generating significant volumes of carbon dioxide after being transferred from the 10° C. bath to the 32° C. bath.

EXAMPLE 9

An additional experiment was carried out to compare the temperature sensitivity of the lts yeasts used in the invention with that fermipan, a commercially available yeast commonly used in dough manufacturing. For each test, 10 samples of the lts yeast culture and 10 samples of the fermipan culture were prepared. Each sample comprised 5 ml of YEPD medium (known in the art) in a test tube, to which a 100 microliter inoculum was added. The test tubes were then plugged at the top with cotton. Five samples of each of the lts strain and the fermipan were placed in incubation at 32° C. while the other five samples of each strain were incubated at 10° C. for about 14 days and then transferred to 32° C. incubation for the remainder of the test. Absorbance readings at a wavelength of about 600 nm were measured periodically over the course of the experiment. The measurements of each of the five samples of a strain at a given condition were averaged together to yield an average reading at that time. Absorbance readings are widely recognized in the art as an accurate measure of yeast population—the absorbance of a yeast culture is generally directly proportional to the number of cells present, i.e., the more yeast cells in the culture, the greater the absorbance.

Figure 21:
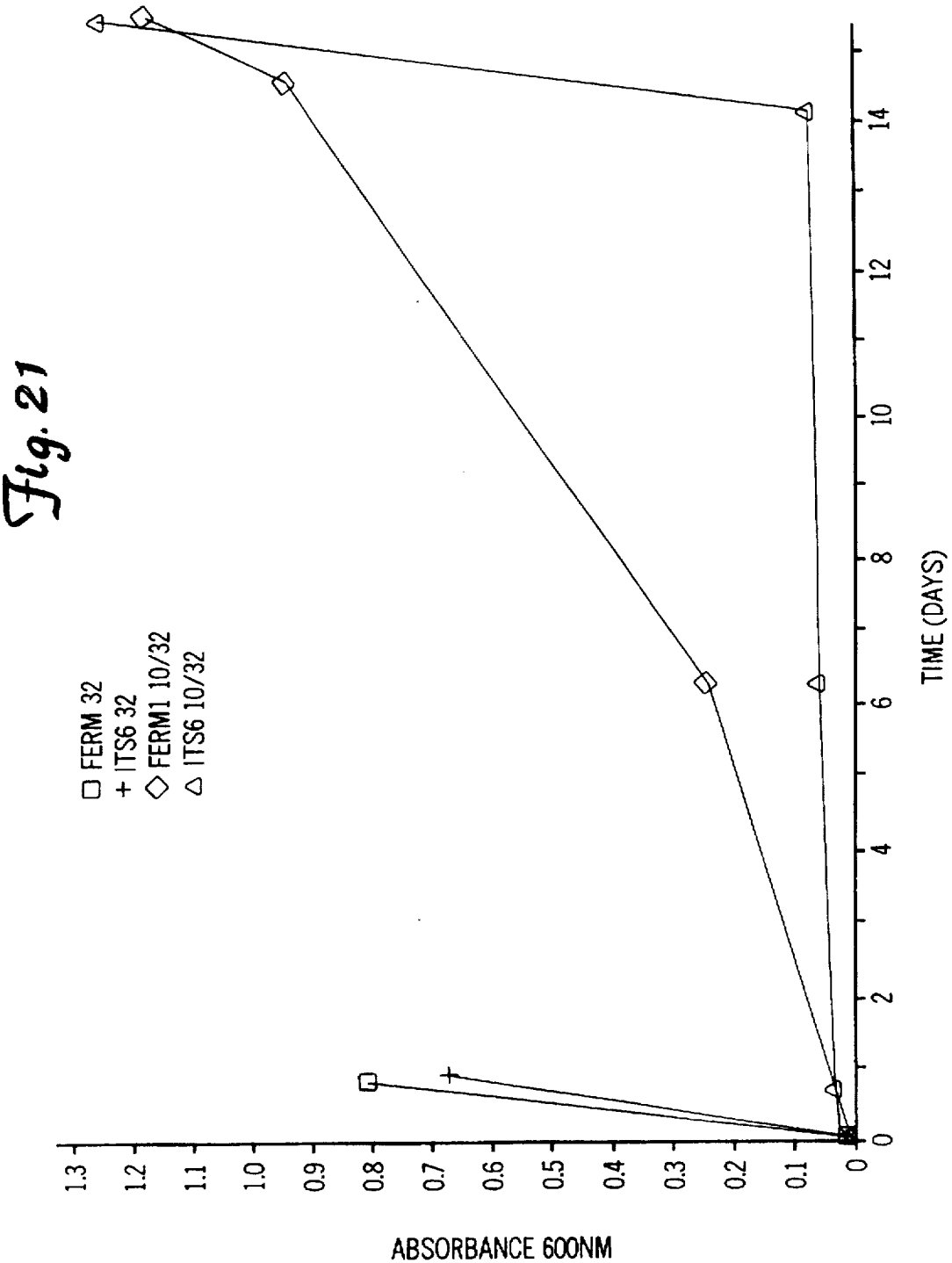
FIG. 21 is a graph showing the absorbance over time for yeast cultures of lts6 yeast and fermipan at 32° C. and at 10° C. then 32° C.
Figure 22:
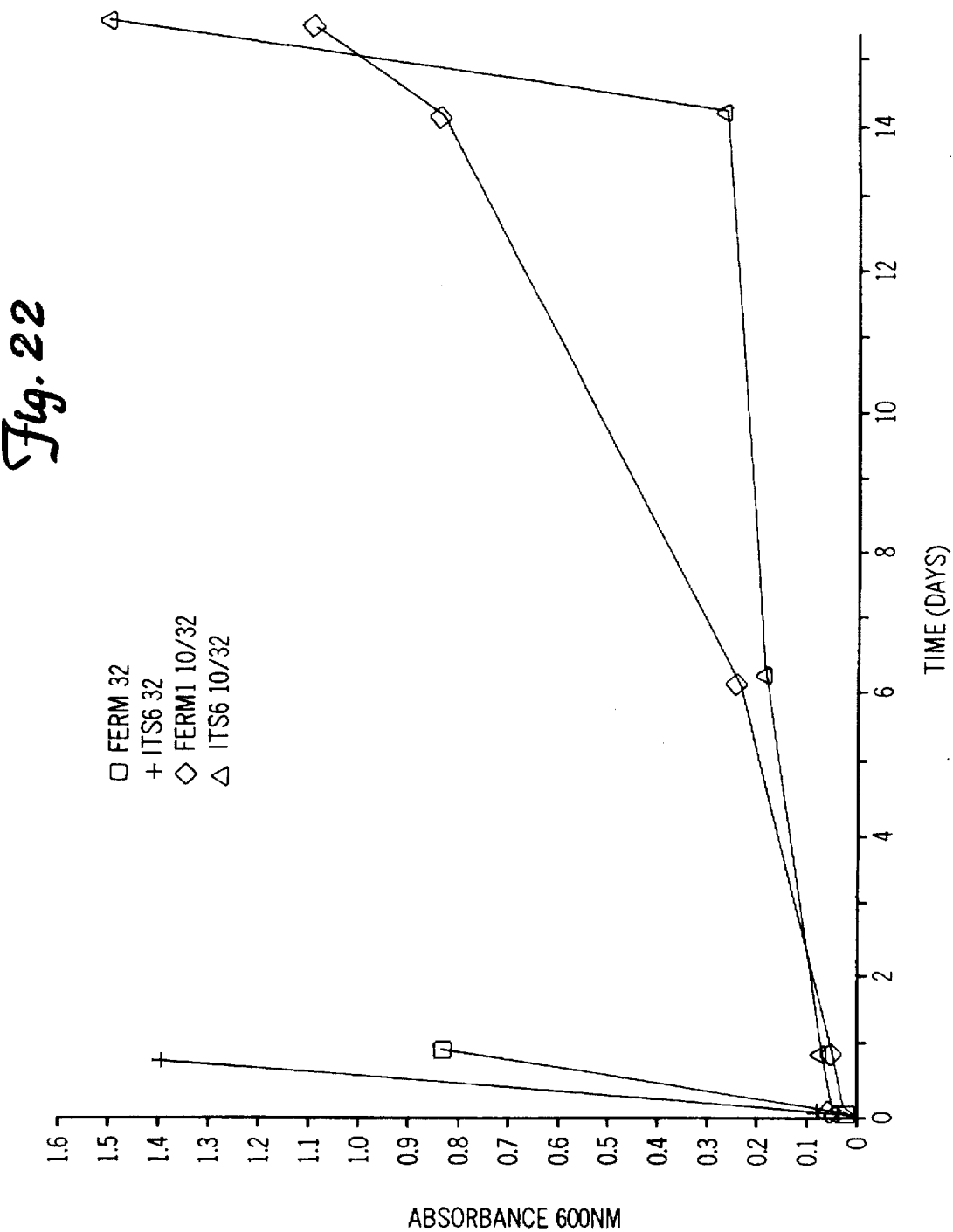
FIG. 22 is a graph showing the absorbance over time for yeast cultures of lts4 yeast and fermipan at 32° C. and at 10° C. then 32° C.

FIGS. 21 and 22 show the results of this testing on the lts6 and lts4 yeasts, respectively. As shown in both of these figures, the lts yeast cultures grew at a rate rather similar to that of the fermipan yeast culture in the samples incubated at 32° C.; both the lts and fermipan yeasts grew rapidly at that temperature.

However, the difference between the lts strains and the fermipan strain was quite noticeable at 10° C. As shown in FIGS. 21 and 22, the fermipan grew at a rate slower than that observed at 32° C., but that nonetheless continued to grow at a relatively fast rate. Both of the lts strains, though, exhibited relatively little or no increase in absorbance over a period of about two weeks at 10° C. This indicates that growth of these strains was significantly inhibited at this temperature. However, both the lts6 and lts4 yeasts grew rather quickly when the incubation temperature was increased to 32° C., proving that they remained viable despite storage for about two weeks at a refrigeration temperature. As expected, the rate of growth of the fermipan also increased upon transfer to the 32° C. incubation environment.

Comparison of the results of the 10° C. incubation for the lts6 yeast (FIG. 21) and that for the lts4 yeast (FIG. 22) is instructive. Although the lts4 yeast grew very slowly at this temperature, it still grew noticeably more than the lts6 yeast over the same period of time. Accordingly, the lts6 strain has been classified as being "high" low temperature sensitive while the lts4 strain has been classified as being only "moderately" low temperature sensitive. That is not to say that the lts4 yeast would not serve as an effective yeast for use in the present invention; to the contrary, as explained below, lts4 is one of the particularly preferred strains for use in the invention. These designations are intended simply as a means for classifying the growth rates of the respective strains isolated in a growth medium, as in this test.

The results of the testing on most of the rest of the lts strains of yeast paralleled those shown in either FIG. 21 or FIG. 22. Based on these results, the lts6, lts1, lts5 and lts8 strains have been classified as being "highly" low temperature sensitive and the lts3, lts4 and lts7 strains have been classified as being "moderately" low temperature sensitive. Of the samples tested, only fermipan, the commercially available baking yeast, can be classified as having "low" low temperature sensitivity; although the growth rate was reduced at refrigeration temperatures, it continued to growth quite rapidly at refrigeration temperatures. With respect to the lts2 yeast, it is believed that a transcription error occurred in carrying out the test because the results indicated that the lts2 yeast's growth rates at both 32° C. and 10° C. were essentially identical to those of fermipan. However, this result is at odds with other testing performed with the lts2 sample (see, e.g., Example 7). Accordingly, the proper classification of the lts2 yeast according to this classification scheme is undetermined at this time.

EXAMPLE 10

Another test was conducted using doughs leavened with lts yeasts according to the invention to evaluate the ability of the doughs to be stored under common commercial conditions. Each dough composition was placed into a separate container and proofed, substantially in accordance with the procedure set forth above in Example 3, then stored at about 35°–50° F. (approximately 2°–10° C.). The dough compositions utilized in the present tests were the same doughs described above in Examples 7 and 8 for the lts2 and lts1 yeast strains, respectively. As explained above, similar dough compositions were prepared using lts4, lts5, lts6, lts7, and lts8 yeast strains, and those doughs were used in the present test as well.

Figure 23:
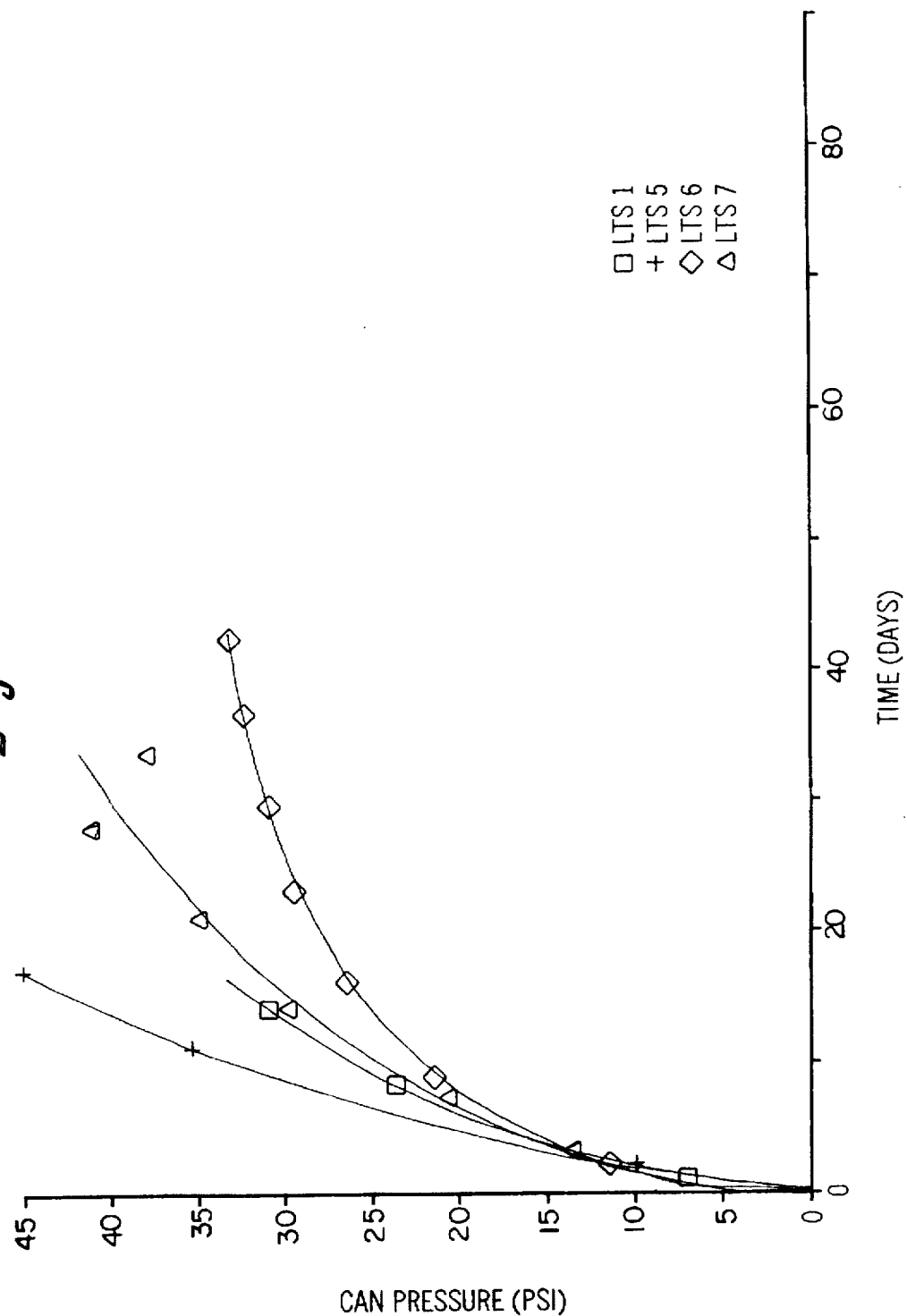
FIG. 23 is a graph showing the pressure within sealed containers containing dough compositions with lts1, lts5, lts6, or lts7 yeast over time at refrigeration temperatures.
Figure 24:
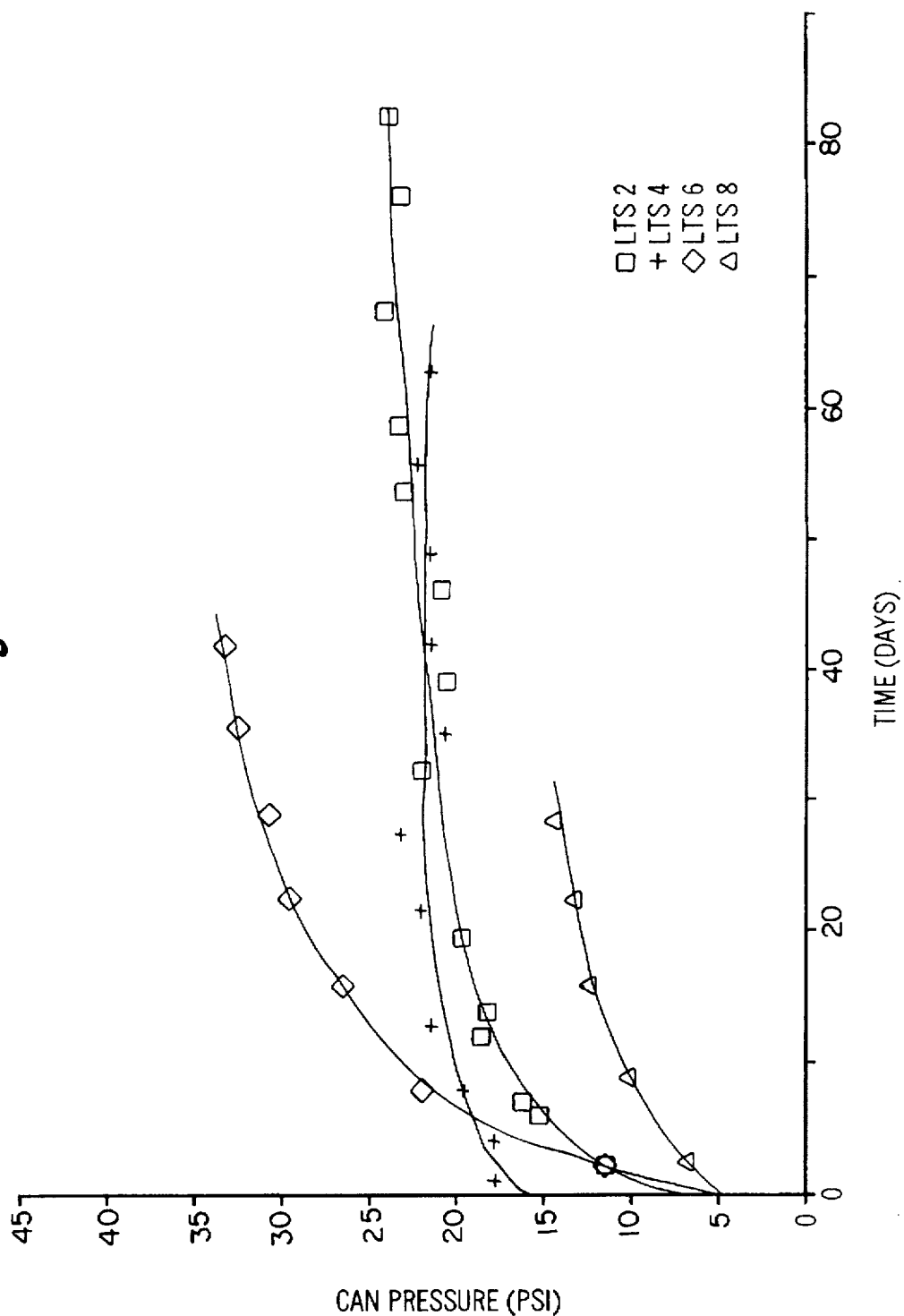
FIG. 24 is a graph showing the pressure within sealed containers containing dough compositions with lts2, lts4, lts6, or lts8 yeast over time at refrigeration temperatures.

As in Example 3, the pressure within each container was monitored over an extended period of time. FIGS. 23 and 24 depict the data collected in this experiment. As previously noted, the pressure limit of most commercial refrigerated dough cans is on the order of about 40–45 psi and the cans will rupture or explode if the pressure significantly exceeds that limit. Accordingly, a dough which is expected to maintain a pressure less than this limit over the commercial shelf life (about 90 days) can be classified as having "good" dough can stability while a dough which is expected to meet or exceed the limit within about 90 days can be classified as having "poor" dough can stability.

FIG. 23 depicts the data collected for samples classified as having "poor" dough can stability while FIG. 24 depicts the results for samples classified as having "good" dough can stability. The lts6 dough sample appears in both FIGS. 23 and 24 because it has been classified as having "moderate" dough can stability—it appears to have leveled off at less than about 35 psi, so the cans should not rupture, but a lower can pressure, e.g. on the order of less than about 25–30 psi, is generally preferred.

Referring first to FIG. 23, it can be seen that the doughs containing lts1, lts5 or lts7 would be expected to meet or exceed the 40–45 psi limit well before the end of 90-day storage at refrigeration temperatures. As a matter of fact, the can with the lts5 dough sample exceeded the 45 psi limit within about 20 days and ruptured during testing. Referring to FIG. 24, though, lts2, lts4, lts6 and lts8 samples all show good dough can stability. With the exception of the lts6 sample, which has been classified as having moderate stability, as noted above, all of the samples maintained dough can pressures of less than about 25 psi, well within acceptable limits for most commercial dough cans.

A dough of the invention may use any lts yeast, as noted above. However, in order to achieve the maximum stable shelf life for the dough without significant risk of rupturing the can, the present experiment indicates that the lts2, lts4, lts6 and lts8 strains are preferred. Furthermore, the lts2, lts4 and lts8 strains are particularly preferred. Viewing the results of this experiment in light of those obtained in Example 9, it is clear that at least lts4, lts6 and lts8 are desirable strains for use in the invention—three of these strains were either "highly" or "moderately" low temperature sensitive, as determined in Example 9, and also showed good dough can stability, as determined in Example 10. Although the results of the tests of Example 9 were inconclusive for lts2 due to an error in conducting the test, one would also expect lts2 to show "high" or "moderate" low temperature sensitivity. Thus, the results of Example 9 confirm the conclusions reached in Example 10 and embodiments of the invention utilizing lts2, lts4, lts6 or lts8 strains of yeast are particularly preferred embodiments of the invention. It is also worth noting that, if one so desired, one could include more than one strain of these yeasts in a dough composition of the invention, although this is not necessary.

While a preferred embodiment of the present invention has been described, it should be understood that various changes, adaptations and modifications may be made therein without departing from the spirit of the invention and the scope of the appended claims.

What is claimed is:

1. A packaged yeast-leavened and yeast-proofed bread dough composition storable at refrigeration temperatures after proofing for a time period of at least about 90 days without package failure comprising selectively lysed yeast cells, water, and flour wherein the selectively lysed yeast cells produce substantially no carbon dioxide when the dough is at a refrigeration temperature of about 10° C. and the selectively lysed yeast cells produce less than about 40% of the carbon dioxide produced by the intact yeast of the species *Saccharomyces cerevisiae* when incubated for about 19 hours at about 32° C.

2. A packaged yeast-leavened and yeast-proofed bread dough product comprising a pressurizable container and a proofed dough adapted for refrigerated storage after proofing for a period of at least about 90 days without container failure therein, said bread dough comprising flour, water, and selectively lysed yeast cells wherein the selectively lysed yeast cells produce less than about 40% of the carbon dioxide produced by the intact yeast cells of the species *Saccharomyces cerevisiae* when incubated for about 19 hours at about 32° C.

3. The dough composition of claim 1 wherein the yeast is present in a concentration of approximately 1%.

4. The dough composition of claim 1 wherein the selectively lysed yeast cells comprise about 95% of yeast in the yeast-leavened-dough.

5. The dough composition of claim 1 wherein the selectively lysed yeast cells comprise about 99% of yeast in the yeast leavened dough.

6. A method for preparing a yeast-leavened and yeast-proofed pressurized refrigerated bread dough product comprising: (a) adding a yeast to chilled water in order to selectively lyse the yeast; (b) preparing a dough by mixing flour, water and the selectively lysed yeast; (c) packaging said dough in a container; (d) proofing said dough in said container; and (e) storing said product at refrigeration temperatures.

7. A method according to claim 6 wherein said proofing step is carried out at greater than ambient temperature.

8. The method according to claim 6 further comprising a step of selecting a yeast which substantially halts carbon dioxide production at refrigeration temperatures.

9. A method of preparing a yeast-leavened and yeast-proofed pressurized refrigerated dough product producing less than 40% of the carbon dioxide than is produced by a dough product prepared with dry intact yeast of the species *Saccharomyces cerevisiae* when incubated for about 19 hours at about 32° C., comprising:

(a) preparing a dough having flour, lysed yeast and water;

(b) packaging said dough in a container;

(c) proofing said dough in said container; and (d) storing said product at refrigerated temperature.

* * * * *